US005853763A

United States Patent [19]
Tice et al.

[11] Patent Number: 5,853,763
[45] Date of Patent: Dec. 29, 1998

[54] METHOD FOR DELIVERING BIOACTIVE AGENTS INTO AND THROUGH THE MUCOSALLY-ASSOCIATED LYMPHOID TISSUE AND CONTROLLING THEIR RELEASE

[75] Inventors: Thomas R. Tice; Richard M. Gilley; John H. Eldridge; Jay K. Staas, all of Birmingham, Ala.

[73] Assignees: Southern Research Institute; The UAB Research Foundation, both of Birmingham, Ala.

[21] Appl. No.: 467,314

[22] Filed: Jun. 6, 1995

Related U.S. Application Data

[63] Continuation of Ser. No. 116,484, Sep. 7, 1993, which is a continuation of Ser. No. 629,138, Dec. 18, 1990, abandoned, which is a continuation-in-part of Ser. No. 325,193, Mar. 16, 1989, abandoned, which is a continuation-in-part of Ser. No. 169,973, Mar. 18, 1988, Pat. No. 5,075,109, which is a continuation-in-part of Ser. No. 923,159, Oct. 24, 1986, abandoned.

[51] Int. Cl.⁶ .......................... A61K 9/52; A61K 39/085; A61K 39/12; A61K 39/39
[52] U.S. Cl. .................. 424/489; 424/184.1; 424/204.1; 424/206.1; 424/234.1; 424/237.1; 424/434; 424/435; 424/436; 424/499; 424/501; 424/810; 514/885; 514/888; 514/963
[58] Field of Search ........................ 428/402.21, 402.24; 424/439, 461, 499, 237.1, 256.1, 434, 497, 810, 435, 501, 489; 514/888, 963, 885, 958; 530/403

[56] References Cited

U.S. PATENT DOCUMENTS

| | | |
|---|---|---|
| 2,738,303 | 3/1956 | Blythe ........................................ 424/458 |
| 3,474,777 | 10/1969 | Figge et al. ........................ 424/489 X |
| 3,823,228 | 7/1974 | Ferris et al. .............................. 424/494 |
| 3,887,699 | 6/1975 | Yolles ........................................ 424/477 |
| 3,959,457 | 5/1976 | Speaker et al. .......................... 424/1.25 |
| 4,021,364 | 5/1977 | Speiser et al. ......................... 428/402.2 |
| 4,107,288 | 8/1978 | Oppenheim et al. .................... 424/499 |
| 4,123,519 | 10/1978 | Tribble et al. .............................. 424/88 |
| 4,148,876 | 4/1979 | Almeida et al. ............................ 424/89 |
| 4,152,413 | 5/1979 | Goodnow ................................. 424/494 |

(List continued on next page.)

FOREIGN PATENT DOCUMENTS

| | | |
|---|---|---|
| 0523028 | 10/1979 | Australia . |
| 0526326 | 7/1980 | Australia . |
| 31088/84 | 1/1985 | Australia . |
| 13700/88 | 10/1988 | Australia . |
| 1023266 | 12/1977 | Canada . |
| 1176565 | 10/1984 | Canada . |
| A 0126537 | 11/1984 | European Pat. Off. . |
| A 0130162 | 1/1985 | European Pat. Off. . |
| 0142192 | 5/1985 | European Pat. Off. . |
| A 0213303 | 3/1987 | European Pat. Off. . |
| 0266119 | 5/1988 | European Pat. Off. . |
| 0286847 | 10/1988 | European Pat. Off. . |
| 0 292 710 | 11/1988 | European Pat. Off. . |
| 2287216 | 6/1976 | France ................................. 424/125 |
| 52-96726/77 | 8/1977 | Japan . |
| 2160312 | 12/1985 | United Kingdom . |
| WO 84/00294 | 2/1984 | WIPO . |
| WO 87/03197 | 6/1987 | WIPO . |
| WO 87/06129 | 10/1987 | WIPO . |
| WO 88/01213 | 2/1988 | WIPO . |
| WO 88/09163 | 12/1988 | WIPO . |
| WO 89/08449 | 9/1989 | WIPO . |

OTHER PUBLICATIONS

Schröeder & Ståhl, *J. Immunol. Methods* 70, 127–132 (1984).

"Biomedical Applications of Microencapsulation", Ed. F. Lim, Chapter 3, pp. 53–58, CRC Press, Boca Raton, FL. (1984).

Langer "Polymers for Release of Macromolecules", Chapter 4 (pp. 57–75) in *Methods in Enzymol.* vol. 73, Immunochemical Techniques, Ed. Langone & Van Vunakis (1981).

Eldridge et al, "New Strategies for Oral Administration", Birmingham, Alabama, as reported in *Current Topics in Microbiology and Immunology*, 146, 59–66, (1989) (Received by the University of Alabama at Birmingham Library on Jun. 12, 1989).

Moldoveanu et al, "New Strategies for Oral Administration", Birmingham, Alabama, as reported in *Current Topics Microbiol. Immunol.* 146, 91–99, (1989) (Received by the University of Alabama at Birmingham Library on Jun. 12, 1989).

Black et al., Immunogenicity of Ty21a Attenuated *Salmonella Typhi* Given With Sodium Bicarbonate or in Enteric--Coated Capsules, *Dev. Biol. Stand.*, vol. 53, pp. 9–14 (1984).

Cox et al., IgA Antibody produced by Local Presentation of Antigen in Orally Primed Rats, *Int.Archs.Allergy Appl.Immun.*, vol. 74, pp. 249–255 (1984).

Deasy, P., Microencapsulation and Related Drug Process, *Drugs and the Pharmaceutical Sciences*, vol. 20, Chapter 1, pp. 8–13 and Chapter 10, pp. 218–227, Ed. James Swarbrick, Marcel Dekker, Inc., New York (1984).

Kondo, A., Applications and Studies of Microcapsules, Chapter 3, pp. 18–20; In–Liquid Curing Coating Process (Orifice Process), Chapter 7, pp. 61 and 68; Microencapsulation Utilizing Phase Separation From an Aqueous Solution System, Chapter 8, pp. 70 and 90–92; Microencapsulation Utilizing In–Liquid Drying Process (Complex Emulstion Method), Chapter 10, pp. 106–109 and 118–119, *Microcapsule Processing and Technology*, Ed. J. Wade Van Walkenburg, Marcel Dekker, Inc., New York (1980).

(List continued on next page.)

*Primary Examiner*—Richard D. Lovering
*Attorney, Agent, or Firm*—Needle & Rosenberg, P.C.

[57] ABSTRACT

A method, and compositions for use therein capable, of delivering a bioactive agent to an animal entailing the steps of encapsulating effective amounts of the agent in a biocompatible excipient to form microcapsules having a size less than approximately ten micrometers and administering effective amounts of the microcapsules to the animal. A pulsatile response is obtained, as well as mucosal and systemic immunity.

52 Claims, 2 Drawing Sheets

U.S. PATENT DOCUMENTS

| | | | |
|---|---|---|---|
| 4,152,414 | 5/1979 | Harris et al. | 424/490 |
| 4,152,415 | 5/1979 | Harris et al. | 424/494 |
| 4,166,800 | 9/1979 | Fong | 427/212 |
| 4,196,188 | 4/1980 | Besins | 424/455 |
| 4,203,968 | 5/1980 | Harris et al. | 424/92 |
| 4,209,507 | 6/1980 | Ogino et al. | 424/116 |
| 4,269,821 | 5/1981 | Kreuter et al. | 424/489 |
| 4,291,016 | 9/1981 | Nougaret | 424/494 |
| 4,292,298 | 9/1981 | Davis . | |
| 4,298,002 | 11/1981 | Ronel et al. | 128/260 |
| 4,309,405 | 1/1982 | Guley et al. | 424/493 |
| 4,309,406 | 1/1982 | Guley et al. | 424/489 |
| 4,326,524 | 4/1982 | Drake, Jr. et al. | 128/260 |
| 4,349,530 | 9/1982 | Royer | 424/486 |
| 4,367,217 | 1/1983 | Gruber et al. | 424/494 |
| 4,384,975 | 5/1983 | Fong | 427/213.36 |
| 4,389,330 | 6/1983 | Tice et al. | 427/213.36 |
| 4,428,925 | 1/1984 | Keith | 424/472 |
| 4,428,926 | 1/1984 | Keith | 424/473 |
| 4,434,153 | 2/1984 | Urguhart et al. | 424/469 |
| 4,439,199 | 3/1984 | Amkraut et al. | 604/894 |
| 4,455,142 | 6/1984 | Martins et al. | 604/890 |
| 4,479,911 | 10/1984 | Fong | 264/4.6 |
| 4,484,923 | 11/1984 | Amkraut et al. | 604/894 |
| 4,524,060 | 6/1985 | Mughal et al. | 424/459 |
| 4,525,339 | 6/1985 | Behl et al. | 424/459 |
| 4,526,938 | 7/1985 | Churchill et al. | 525/415 |
| 4,530,840 | 7/1985 | Tice et al. | 514/179 |
| 4,542,025 | 9/1985 | Tice et al. | 424/78 |
| 4,559,303 | 12/1985 | Aotani et al. | 435/180 |
| 4,585,651 | 4/1986 | Beck et al. | 424/88 |
| 4,590,170 | 5/1986 | Akiyoshi et al. | 436/533 |
| 4,610,870 | 9/1986 | Jain et al. | 424/465 |
| 4,613,500 | 9/1986 | Suzuki et al. | 424/85 |
| 4,650,769 | 3/1987 | Kakimi et al. | 436/533 |
| 4,657,756 | 4/1987 | Rasor et al. | 424/9 |
| 4,681,752 | 7/1987 | Melillo | 424/453 |
| 4,690,682 | 9/1987 | Lim | 604/891 |
| 4,732,763 | 3/1988 | Beck et al. | 424/433 |
| 4,764,359 | 8/1988 | Lemelson | 424/1.1 |
| 4,783,336 | 11/1988 | Margel et al. | 424/462 |
| 4,845,042 | 7/1989 | Newman et al. | 436/545 |
| 4,919,929 | 4/1990 | Beck | 424/88 |
| 4,925,673 | 5/1990 | Steiner et al. | 424/455 |
| 4,990,336 | 2/1991 | Silvestri et al. | 424/426 |
| 5,075,109 | 12/1991 | Tice et al. | 424/88 |
| 5,126,147 | 6/1992 | Silvestri et al. | 424/497 |
| 5,384,133 | 1/1995 | Boyes et al. | 424/501 |
| 5,417,986 | 5/1995 | Reid et al. | 424/499 |
| 5,503,841 | 4/1996 | Doyle et al. | 424/278.1 |

OTHER PUBLICATIONS

Kreuter et al., New Adjuvants on a Polymethymethacrylate Base, *Infection and Immunity*, vol. 13, pp. 204–210 (Jan. 1976).

Kreuter et al., Long–Term Studies of Microencapsulated and Adsorbed Influenza Vaccine Nanparticles, *J.Pharm.Sci.*, vol. 70, No. 4, pp. 367–371 (Apr. 1981).

Lazzell et al., Immunization Against Influenza in Humans Using an Oral Enteric–Coated Killed Virus Vaccine, *J.Biol.Standardization*, vol. 12, pp. 315–321 (1984).

Preis et al., A Single–Step Immunization by Sustained Antigen Release, *J.Immun.Methods*, vol. 28, pp. 193–197 (1979).

Saffran et al., A New Approach to the Oral Administration of Insulin and Other Peptide Drugs, *Science*, vol. 233, pp. 1081–1085 (Sep. 5, 1986).

Sanders et al., Controledl Release of a Luteinizing Hormone–Releasing Hormone Analogue from Poly(d,1–lactide–co–glycolide) Microspheres, *J.Pharm.Sci.*, vol. 73, No. 9, pp. 1294–1297 (Sep. 1984).

Shigeta et al., Plasma Immunoreactive Insulin After Intestinal Administration of β–Naphthyl–Azo–Polystyrene–Insulin to the Rabbit, *Endocrinology, Notes and Comments*, vol. 91, No. 1, pp. 320–322 (1972).

Artursson et al., "Characterization of Polyacryl Starch Microparticles as Carriers for Proteins and Drugs," *J.Pharm.Sci.*, vol. 73, No. 11, pp. 1507–1513 (Nov. 1984).

Artursson et al., "Biodegradable Microspheres II: Immune Response to a Heterologous and an Autologous Protein Entrapped in Polyacryl Starch Microparticles," *J.Pharm.&Exp.Ther.*, vol. 234, No.1, pp. 255–260 (1985).

Artursson et al., Biochemical and Cellular Effects of Degraded Starch Microspheres on Macrophages, *Intl.J.Pharm.*, vol. 52, pp. 183–190 (1989).

Barratt et al., "Delivery of MDP–L–alanyl–cholesterol to Macrophages: Comparison of Liposomes and Nanocapsules," *The Cancer Journal*, vol. 2, No. 12, pp. 439–443 (Nov./Dec. 1989).

Chang, T., "Biodegradable Semipermeable Microcapsules Containing Enzymes, Hormones, Vaccines, and Other Biologicals," *J.Bioeng.*, vol. 1, pp. 25–32 (1976).

Cox et al., "Oral Induction of the Secretory Antibody Response by Soluble and Particulate Antigens," *Int.Archs.AllergyAppl.Immun.*, vol. 75, pp. 126–131 (1984).

Damgé et al., "New Approach for Oral Administration of Insulin with Polyalkylcyanoacrylate Nanocapsules as Drug Cattier," *Diabetes*, vol. 37, pp. 246–251 (Feb. 1988).

DeLuca et al., "Porous Biodegradable Microspheres for Parenteral Administration," *Topics Pharm.Sci.* 1987, D. Breimer et al., eds., pp. 429–442 (Aug./Sep. 1987).

Gundel et al., "Antigen–Coated Sepharose Beads Induce Airway Eosinophilia and Airway Hyperesponsiveness in Cynomolgus Moneys," *Am.Rev.Respir.Dis.*, vol. 140, pp. 629–633 (1989).

Harmia et al., "The Role of Macrophages in Particle Translocation from Lungs to Lymph Nodes," *Science*, vol. 230, No. 4731, pp. 1277–1281 (Dec. 1985).

Harmsen et al., "The Role of Macrophages in Particle Translocation from Lungs to Lymphs Nodes," *Science*, vol. 230, No. 4731, pp. 1277–1281 (Dec. 1985).

Hay et al., "The Use of Radioactive Microspheres to Quantitate Hyperemia in Dermal Inflammatory Sites," *Proceedings of the Society for Experimental Biology and Medicine*, vol. 150, pp. 641–644 (Oct.–Dec. 1975).

Hill et al., "Cell–Mediated Immunity to Soluble and Particulate Inhaled Antigens," *Chem.Exp.Immunol., Blackwell Scientific Publications*, vol. 38, pp. 332–341 (1979).

Illum et al., "Bioadhesive Microspheres as a Potential Nasal Drug Delivery System," *Int.J.Pharm.*, vol. 39 pp. 189–199 (1987).

Juliano et al., "The Effect of Particle Size and Charge on the Clearance Rates of Liposomes and Liposome Encapsulated Drugs," *Biochem.&Biophys.Res.Comm.*, P. Boyer et al., eds., vol. 63, No. 3, pp. 651–659 (1975).

Kanke et al., "Interaction of Microspheres with Blood Constituents and the Effect on Immune Response," *Expo–Congr.Int.Technol.Pharm.3d.*, vol. 4, pp. 162–169 (1983).

Kanke et al., "Interaction of Microspheres with Blood Constituents II: Uptake of Biodegradable Particles by Macrophages," *J.Parenteral Sci.&Tech.*, vol. 40, No. 4, pp. 114–118 (Jul./Aug. 1986).

Kante et al., "Interaction of Microspheres with Blood Constituents III: Macrophage Phagocytosis of Various Types of Polymeric Drug Carriers," *J.Parenteral Sci.&Tech.*, vol. 42, No. 5, pp. 157–165 (Sep./Oct. 1988).

Klipstein et al., "Peroral Immunization of Rats with *Escherichia coli* Heat Labile Enterotoxin Delivered by Microspheres, *Infection and Immunity*," vol. 39, No.2, pp. 1000–1003 (Jan. 1983).

Langenback et al., "Supramicron–sized Particle Clearance from Alveoli: Route and Kinetics," *Amer.Physio.Soc.*,. pp. 1302–1308 (1990).

LeFevre et al., "Intestinal Barrier to Large Particulates in Mice," *J.Toxic.&Envir.Health*, vol. 6, pp. 691–704 (1980).

LeFevre et al., "Accumulation of Latex in Peyer's Patches and Its Subsequent Appearance in Villi and Mesenteric Lymph Nodes," *Proceedings of the Society for Experimental Biology & Medicine*, vol. 159, pp. 298–302 (1978).

Lehnert et al., "Leukocytic Responses to the Intrapleural Deposition of particles, Particle–Cell Associations, and the Clearance of Particles From the Pleural Space Compartment," *J.Toxic.&Envir.Health*, vol. 24, pp. 41–66 (1988).

Margel et al., "Polyacrolein Microspheres As a New Tool in Cell Biology," *J.Cell Sci.*, Grimstone et al., vol. 56, pp. 157–175 (1982).

Moldoveanu et al., "Oral Immunization with Influenza Virus in Biodegradable Microspheres," *J.Infect.Dis.*, vol. 167, pp. 001–007 (Sep. 27, 1992).

Nishimura et al., "Effect of Multiporous Microspheres Derived from Chitin and Partially Deacetylated Chitin on the Activation of Mouse Peritoneal Macrophages," *Vaccine*, vol. 5, pp. 136–140 (Jun. 1987).

O'Hagan et al., "Intestinal Absorption of Proteins and Macromolecules and the Immunological Response," *CRC Critical Reviews in Therapeutic Drug Carrier Systems*, vol. 4, Issue 3, pp. 197–220 (1987).

O'Hagan et al., "Poly(butyl–2–cyanoacrylate) Particles As Adjuvants for Oral Immunization," *Vaccine*, vol. 7, pp. 213–216 (Jun. 1989).

O'Hagan et al., "Absorption of Peptides and Proteins from the Respiratory Tract and the Potential for Development of Locality Administered Vaccine," *Critical Reviews in Therapeutic Drug Carrier Systems*, vol. 7, Issue 1, pp. 35–97 (Jan. 1990).

O'Hagan et al., "Intestinal Translocation of Particulates — Implications for Drug and Antigen Delivery," *Adv.Drug Deliv.Rev.*, vol. 5, pp. 265–285 (1990).

Ostro, "Liposomes," *Sci.Amer.*, pp. 102–111 (1987).

Ostroff et al., "Macrophage–Targeted Polysaccharide Microcapsules for Antigen and Drug Delivery," Polymer Reprints: *Am.Chem.Soc., Div.Polym.Chem.*, vol. 31(2), pp. 200–201 (1990).

Read et al., "Gastrointestinal Dynamics and Pharmacology for the Optimum Design of Controlled–Release Oral Dosage Forms," *CRC Critical Reviews in Therapeutic Drug Carrier Systems*, vol. 4, Issue 3, pp. 221–263 (1987).

Sass et al., "Rapid Insorption of Small Particles in the Gut," *Am.J.Gastro.*, vol. 85, No. 3, pp. 255–260 (Mar. 1990).

Svartengren et al., "Human Lung Deposition of Particles Suspended in Air or in Helium/Oxygen Mixture," *Exp.LungRes.*, vol. 15, pp. 575–585 (1989).

Tabata et al., "Macrophage Activation Through Phagocytosis of Muramyl Dipeptide Encapsulated in Gelatin Microspheres," *J.Pharm.Pharmacol.*, vol. 39, pp. 698–704 (1987).

Tabata et al., "Activation of Macrophage In Vitro to Acquire Antitumor Activity by a Muramyl Dipeptide Derivative Encapsulated in Microspheres Composed of Lactide Copolymer," *J.Contr.Rel.*, vol. 6, pp. 189–204 (1987).

Tabata et al., "Phagocytosis of Polymer Microspheres by Macrophanges," *Advances in Polymer Science* 94, pp. 107–141 (1990).

Tabata et al., "Macrophage Phagocytosis of Biodegradable Microspheres Composed of L–lactic Acid/Glycolic Acid Homo–and Copolymers," *J.Biomed.Mat.Res.*, vol. 22, pp. 837–858 (1988).

METHOD FOR DELIVERING BIOACTIVE AGENTS INTO AND THROUGH THE MUCOSALLY-ASSOCIATED LYMPHOID TISSUE AND CONTROLLING THEIR RELEASE

REFERENCE TO CO-PENDING APPLICATION

This application is a continuation of application Ser. No. 08/116,484, filed Sep. 7, 1993, which is a continuation of application Ser. No. 07/629,138, filed Dec. 18, 1990, now abandoned, which is a continuation-in-part of application Ser. No. 07/325,193, filed Mar. 16, 1989, now abandoned, which is a continuation-in-part of application Ser. No. 07/169,973, filed Mar. 18, 1988, now U.S. Pat. No. 5,075,109, which is a continuation-in-part of application Ser. No. 06/923,159, filed Oct. 24, 1986, now abandoned.

This invention was made with government support under Contract No. DAMD17-86-C-6162 awarded by the Department of the Army of the United States Government. The U.S. Government has certain non-commercial rights in the invention. The U.S. Government does not have rights in the invention pertaining to drug delivery.

TABLE OF CONTENTS
BACKGROUND OF THE INVENTION
SUMMARY OF THE INVENTION
BRIEF DESCRIPTION OF THE FIGURES
DETAILED DESCRIPTION OF THE INVENTION
  I. MICROENCAPSULATION
    A. Preparation of Dye-Loaded Microcapsules.
    B. Preparation of Antigen-Loaded Microcapsules.
  II. PENETRATION OF DYE-LOADED MICROCAPSULES INTO THE PEYER'S PATCHES AFTER ORAL ADMINISTRATION
    EXAMPLE 1—Polystyrene Microcapsules.
    EXAMPLE 2—85:15 Poly(DL-lactide-co-glycolide) Microcapsules.
      1. Uptake of Biocompatible and Biodegradable Microcapsules into the Peyer's Patches.
      2. Microcapsule Migration to the Mesenteric Lymph Nodes and Spleen.
    EXAMPLE 3—Comparison of the Uptake of Microcapsules of 10 Compositions by the Peyer's Patches.
  III. ANTIBODY RESPONSES INDUCED WITH MICROENCAPSULATED VACCINES
    MATERIALS AND METHODS
      Trinitrophenyl—Keyhole Limpet Hemocyanin.
      Immunizations.
      Collection of Biological Fluids.
      1. Plasma.
      2. Intestinal Secretions.
      3. Saliva.
      4. Bronchial-Alveolar Wash Fluids.
      5. Immunochemical Reagents.
      6. Solid-Phase Radioimmunoassays.
    A. Vaccine-Microcapsules Administered by Injection.
      1. Adjuvant Effect Imparted by Microencapsulation.
        EXAMPLE 1—Adjuvant Effect Imparted by Microencapsulation-Intraperitoneal Administration.
        EXAMPLE 2—Adjuvant Effect Imparted by Microencapsulation-Subcutaneous Administration.
      2. Mechanism of the Adjuvant Effect Imparted by Microencapsulation.
        EXAMPLE 1—The Adjuvant Effect Imparted by Microencapsulation is Not the Result of Adjuvant Activity Intrinsic to the Polymer.
        EXAMPLE 2—Retarding the Antigen Release Rate from 1–10 Micrometer Microcapsules Increases the Level of the Antibody Response and Delays the Time of the Peak Response.
        EXAMPLE 3—Correlation of the Size of the Microcapsules with the Resultant Adjuvant Effect.
      3. Pulsatile Release of Vaccines from Microcapsules for Programmed Boosting Following a Single Injection
        EXAMPLE 1—Co-administration of Free and Microencapsulated Vaccine.
        EXAMPLE 2—Co-administration of <10 Micrometer Priming and >10 Micrometer Pulsing Vaccine Microcapsules.
        EXAMPLE 3—Co-administration of <10 Micrometer Priming and <10 Micrometer Pulsing Vaccine Microcapsules.
    B. Vaccine-Microcapsules Administered Orally
      EXAMPLE 1—Orally Administered Microspheres Containing TNP-KLH Induce Concurrent Circulating and Mucosal Antibody Responses to TNP.
      EXAMPLE 2—Orally Administered Microcapsules Containing SEB Toxoid Induce Concurrent Circulating and Mucosal Anti-SEB Toxin Antibodies.
    C. Vaccine Microcapsules Administered Intratracheally.
      EXAMPLE 1—Intratracheally Administered Microcapsules Containing SEB Toxoid Induce Concurrent Circulating and Mucosal Anti-Toxin Antibodies.
    D. Vaccine Microcapsules Administered by Mixed Immunization Routes.
  IV. ABSORPTION OF PHARMACEUTICALS.

BACKGROUND OF THE INVENTION

This invention relates to a method and a formulation for orally administering a bioactive agent encapsulated in one or more biocompatible polymer or copolymer excipients, preferably a biodegradable polymer or copolymer, affording microcapsules which due to their proper size and physical chemical properties results in the microcapsules and contained agent reaching and being effectively taken up by the folliculi lymphatic aggregati, otherwise known as the "Peyer's patches", of the gastrointestinal tract in an animal without loss of effectiveness due to the agent having passed through the gastrointestinal tract. Similar folliculi lymphatic aggregati can be found in the respiratory tract, genitourinary tract, large intestine and other mucosal tissues of the body such as ophthalmic tissues. Hereafter, the above-described tissues are referred to in general as mucosally-associated lymphoid tissues.

The use of microencapsulation to protect sensitive bioactive agents from degradation has become well-known. Typically, a bioactive agent is encapsulated within any of a number of protective wall materials, usually polymeric in nature. The agent to be encapsulated can be coated with a single wall of polymeric material (microcapsules), or can be homogeneously dispersed within a polymeric matrix (microspheres). (Hereafter, the term microcapsules refers to both microcapsules and microspheres). The amount of agent inside the microcapsule can be varied as desired, ranging from either a small amount to as high as 95% or more of the microcapsule composition. The diameter of the microcapsule can also be varied as desired, ranging from less than one micrometer to as large as three millimeters or more.

Peyer's patches are aggregates of lymphoid nodules located in the wall of the small intestine, large intestine and appendix and are an important part of body's defense against the adherence and penetration of infectious agents and other substances foreign to the body. Antigens are substances that induce the antibody-producing and/or cell-mediated immune systems of the body, and include such things as foreign protein or tissue. The immunologic response induced by the interaction of an antigen with the immune system may be either positive or negative with respect to the body's ability to mount an antibody or cell-mediated immune response to a subsequent reexposure to the antigen. Cell-mediated immune responses include responses such as the killing of foreign cells or tissues, "cell-mediated cytoxicity", and delayed-type hypersensitivity reactions. Antibodies belong to a class of proteins called immunoglobulins (Ig), which are produced in response to an antigen, and which combine specifically with the antigen. When an antibody and antigen combine, they form a complex. This complex may aid in the clearance of the antigen from the body, facilitate the killing of living antigens such as infectious agents and foreign tissues or cancers, and neutralize the activity of toxins or enzymes. In the case of the mucosal surfaces of the body the major class of antibody present in the secretions which bathe these sites is secretory immunoglobulin A (sIgA). Secretory IgA antibodies prevent the adherence and penetration of infectious agents and other antigens to and through the mucosal tissues of the body.

While numerous antigens enter the body through the mucosal tissues, commonly employed immunization methods, such as intramuscular or subcutaneous injection of antigens or vaccines, rarely induce the appearance of sIgA antibodies in mucosal secretions. Secretory IgA antibodies are most effectively induced through direct immunization of the mucosally-associated lymphoid tissues, of which the Peyer's patches of the gastrointestinal tract represent the largest mass in the body.

Peyer's patches possess IgA precursor B cells which can populate the lamina propria regions of the gastrointestinal and upper respiratory tracts and differentiate into mature IgA synthesizing plasma cells. It is these plasma cells which actually secrete the antibody molecules. Studies by Heremans and Bazin measuring the development of IgA responses in mice orally immunized with antigen showed that a sequential appearance of antigen-specific IgA plasma cells occurred, first in mesenteric lymph nodes, later in the spleen, and finally in the lamina propria of the gastrointestinal tract (Bazin, H., Levi, G., and Doria, G. Predominant contribution of IgA antibody-forming cells to an immune response detected in extraintestinal lymphoid tissues of germ free mice exposed to antigen via the oral route. J. Immunol. 105:1049; 1970 and Crabbe, P. A., Nash, D. R., Bazin, H., Eyssen, H. and Heremans, J. F. Antibodies of the IgA type in intestinal plasma cells of germ-free mice after oral or parenteral immunization with ferritin. J. Exp. Med. 130:723; 1969). Subsequent studies have shown that oral administration of antigens leads to the production of sIgA antibodies in the gut and also in mucosal secretions distant to the gut, e.g., in bronchial washings, colostrum, milk, saliva and tears (Mestecky, J., McGhee, J. R., Arnold, R. R., Michalek, S. M., Prince, S. J. and Babb, J. L. Selective induction of an immune response in human external secretions by ingestion of bacterial antigen. J. Clin. Invest. 61:731; 1978, Montgomery, P. C., Rosner, B. R. and Cohen, J. The secretory antibody response. Anti-DNP antibodies induced by dinitrophenylated Type III pneumococcus. Immunol. Commun. 3:143; 1974, and Hanson, L. A., Ahistedt, S., Carlsson, B., Kaijser, B., Larsson, P., MattsbyBaltzer, A., Sohl Akerlund, A., Svanborg Eden, C. and Dvennerholm, A. M. Secretory IgA antibodies to enterobacterial virulence antigens: their induction and possible relevance, Adv. Exp. Med. Biol, 1007:165; 1978). It is apparent, therefore, that Peyer's patches are an enriched source of precursor IgA cells, which, subsequent to antigen sensitization, follow a circular migrational pathway and account for the expression of IgA at both the region of initial antigen exposure and at distant mucosal surfaces. This circular pattern provides a mucosal immune system by continually transporting sensitized B cells to mucosal sites for responses to gut-encountered environmental antigens and potential pathogens.

Of particular importance to the present invention is the ability of oral immunization to induce protective antibodies. It is known that the ingestion of antigens by animals results in the appearance of antigen-specific sIgA antibodies in bronchial and nasal washings. For example, studies with human volunteers show that oral administration of influenza vaccine is effective at inducing secretory anti-influenza antibodies in nasal secretions.

Extensive studies have demonstrated the feasibility of oral immunization to induce the common mucosal immune system, but with rare exception the large doses require to achieve effective immunization have made this approach impractical. It is apparent that any method or formulation involving oral administration of an ingredient be of such design that will protect the agent from degradation during its passage through the gastrointestinal tract and target the delivery of the ingredient to the Peyer's patches. If not, the ingredient will reach the Peyer's patches, if at all, in an inadequate quantity or ineffective condition.

Therefore, there exists a need for a method of oral immunization which will effectively stimulate the immune system and overcome the problem of degradation of the antigen during its passage through the gastrointestinal tract to the Peyer's patch. There exists a more particular need for a method of targeting an antigen to the Peyer's patches and releasing that antigen once inside the body. There also exists a need for a method to immunize through other mucosal tissues of the body which overcomes the problems of degradation of the antigen and targets the delivery to the mucosally-associated lymphoid tissues. In addition, the need exists for the protection from degradation of mucosally applied bioactive agents, improves and/or targets their entrance into the body through the mucosally-associated lymphoid tissues and releases the bioactive agent once it has entered the body.

SUMMARY OF THE INVENTION

This invention relates to a method and formulation for targeting to and then releasing a bioactive agent in the body of an animal by mucosal application, and in particular, oral and intratracheal administration. The agent is microencapsulated in a biocompatible polymer or copolymer, preferably a biodegradable polymer or copolymer which is capable of passing through the gastrointestinal tract or existing on a mucosal surface without degradation or with minimal degradation so that the agent reaches and enters the Peyer's patches or other mucosally-associated lymphoid tissues unaltered and in effective amounts. The term biocompatible is defined as a polymeric material which is not toxic to the body, is not carcinogenic, and which should not induce inflammation in body tissues. It is preferred that the microcapsule polymeric excipient be biodegradable in the sense that it should degrade by bodily processes to products readily disposable by the body and should not accumulate in the body. The microcapsules are also of a size and physicalchemical composition capable of being effectively and selectively taken up by the Peyer's patches. Therefore, the problems of the agent reaching the Peyer's patch or other mucosally-associated tissue and being taken up are solved.

It is an object of this invention to provide a method of orally administering an antigen to an animal which results in the antigen reaching and being taken up by the Peyer's patches, and thereby stimulating the mucosal immune system, without losing its effectiveness as a result of passing through the animal's gastrointestinal tract.

It is also an object of this invention to provide a method of orally administering an antigen to an animal which results in the antigen reaching and being taken up by the Peyer's patches, and thereby stimulating the systemic immune system, without losing its effectiveness as a result of having passed through the gastrointestinal tract.

It is a further object of this invention to provide a method of administering an antigen to an animal which results in the antigen reaching and being taken up by the mucosally-associated lymphoid tissues, and thereby stimulating the mucosal immune system, without losing its effectiveness as a result of degradation on the mucosal surface.

It is a still further object of this invention to provide a method of administering an antigen to an animal which results in the antigen being taken up by the mucosally-associated lymphoid tissues, and thereby stimulating the systemic immune system, without losing its effectiveness as-a result of degradation on the mucosal surface.

It is a still further object of this invention to provide a method of orally administering a bioactive agent to an animal which results in the agent reaching and being taken up by the Peyer's patches, and thereby resulting in an increased local or systemic concentration of the agent.

It is a still further object of this invention to provide a method of administering a bioactive agent to an animal which results in the agent reaching and being taken up by the mucosally-associated lymphoid tissues, and thereby resulting in an increased local or systemic concentration of the agent.

It is a still further object of this invention to provide a formulation consisting of a core bioactive ingredient and an encapsulating polymer or copolymer excipient which is biocompatible and preferably biodegradable as well, which can be utilized in the mucosal-administration methods described above.

It is another object of this invention to provide an improved vaccine delivery system which obviates the need for immunopotentiators.

It is a still further object of this invention to provide an improved vaccine delivery system for the induction of immunity through the pulsatile release of antigen from a single administration of microencapsulated antigen.

It is a still further object of this invention to provide an improved vaccine delivery system which both obviates the need for immunopotentiators and affords induction of immunity through pulsatile releases of antigen all from a single administration of microcapsulated antigen.

It is a further object of this invention to provide a composition capable of achieving these above-referenced objects

DETAILED DESCRIPTION OF THE INVENTION

Figure 1:
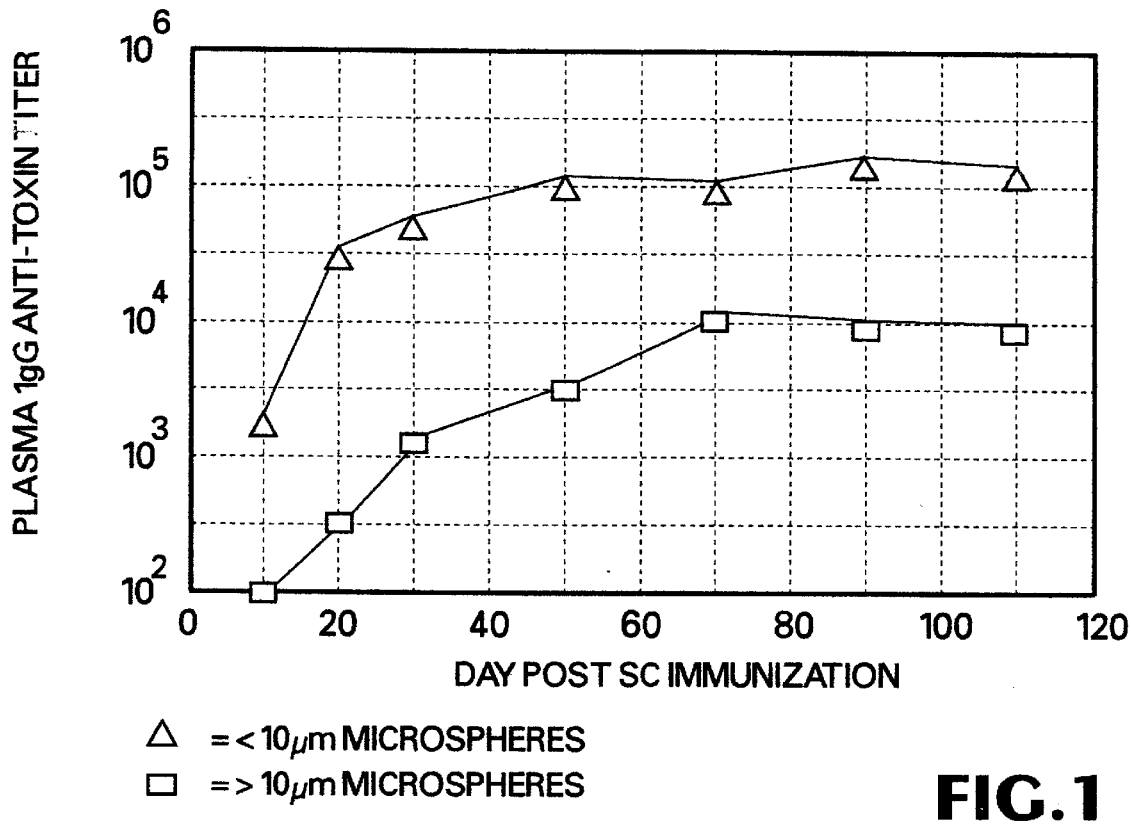
FIG. 1 represents the plasma IgG responses in mice following subcutaneous administration of 1–10 $\mu$m and 10–110 $\mu$m 85:15 DL-PLG SEB toxoid-containing microspheres.
Figure 2:
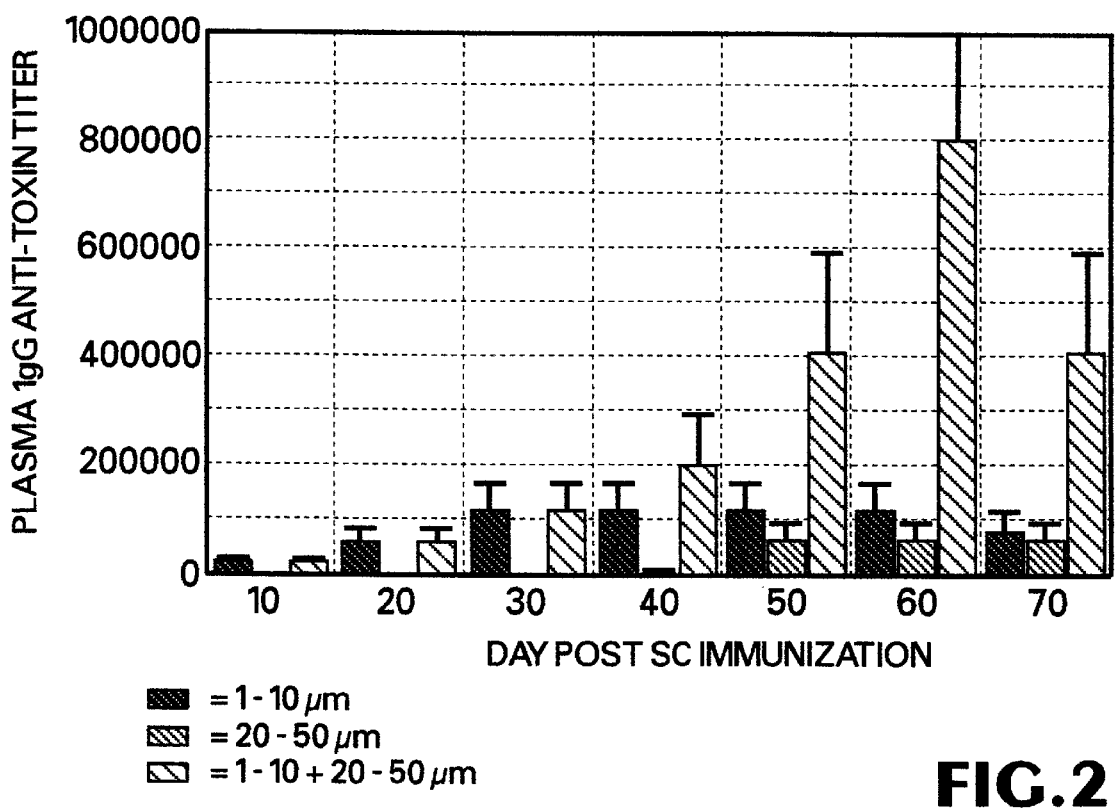
FIG. 2 represents the plasma IgG responses in mice determined by endpoint titration following subcutaneous administration of 1–10 $\mu$m, 20–50 $\mu$m and a mixture of 1–10 and 20–50 $\mu$m SEB toxoid-containing microcapsules.

Illustrations of the methods performing embodiments of the invention follow. These illustrations demonstrate the mucosally-associated lymphoid tissue targeting and programmed delivery of the antigens (trinitrophenyl keyhole limpet hemocyanin and a toxoid vaccine of staphylococcal enterotoxin B), and a drug (etretinate) encapsulated in 50:50 poly(DL-lactide-co-glycolide) to mice.

It should be noted, however, that other polymers besides poly(DL-lactide-co-glycolide) may be used. Examples of such polymers include, but are not limited to, poly (glycolide), poly(DL-lactide-co-glycolide), copolyoxalates, polycaprolactone, poly(lactide-co-caprolactone), poly (esteramides), polyorthoesters and poly(B-hydroxybutyric acid), and polyanhydrides.

Also, other bioactive ingredients may be used. Examples of such include, but are not limited to, antigens to vaccinate against viral, bacterial, protozoan, fungal diseases such as influenzae, respiratory syncytial, parainfluenza viruses, Hemophilus influenza, Bordetella pertussis, Neisseria gonorrhoeae, Streptococcus pneumoniae and Plasmodium falciparum or other diseases caused by pathogenic microorganisms or antigens to vaccinate against diseases caused by macroorganisms such as helminthic pathogens or antigens to vaccinate against allergies. Additional bioactive agents which may be used included but are not limited to, immunomodulators, nutrients, drugs, peptides, lymphokines, monokines and cytokines.

I. MICROENCAPSULATION

A. Preparation of Dye-Loaded Microcapsules

Coumarin, a water-insoluble fluorescent dye, was microencapsulated with polystyrene, which is a nonbiodegradable polymer, to afford fluorescent microcapsules that could be used to follow the penetration of microcapsules into the Peyer's patches. The procedure used to prepare these microcapsules follows:

First, a polymer solution is prepared by dissolving 4.95 g of polystyrene (Type 685D, Dow Chemical Company, Midland, Mich.) in 29.5 g of methylene chloride (Reagent Grade, Eastman Kodak, Rochester, N.Y.). Next, about 0.05 g of coumarin (Polysciences, Inc., Warrington, Pa.) is added to the polymer solution and allowed to dissolve by stirring the mixture with a magnetic stir bar.

In a separate container, 10 wt % aqueous poly(vinyl alcohol) (PVA) solution, the processing medium, is prepared by dissolving 40 g of PVA (Vinol 2050, Air Products and Chemicals, Allentown, Pa.) in 360 g of deionized water. After preparing the PVA solution, the solution is saturated by adding 6 g of methylene chloride. Next, the PVA solution is added to a 1-L resin kettle (Ace Glass, Inc., Vineland, N.J.) fitted with a truebore stir shaft and a 2.5-in. TEFLON impeller and stirred at about 380 rpm by a Fisher stedi speed motor.

The polystyrene/coumarin mixture is then added to the resin kettle containing the PVA processing media. This is accomplished by pouring the polystyrene/coumarin mixture through a long-stem 7-mm bore funnel which directs the mixture into the resin kettle. A stable oil-in-water emulsion results and is subsequently stirred for about 30 minutes at ambient pressure to afford oil microdroplets of the appropriate size. Then the resin kettle is closed, and the pressure in the resin kettle is gradually reduced to 520 mm Hg by means of a water aspirator connected to a manometer and a bleed valve. The resin kettle contents are stirred at reduced pressure for about 24 hours to allow all of the methylene chloride to evaporate. After all of the methylene chloride has evaporated, the hardened microcapsules are collected by centrifugation and dried for 72 hours in a vacuum chamber maintained at room temperature.

B. Preparation of Antigen-Loaded Microcapsules

TNP-KLH, a water-soluble antigen, was encapsulated in poly(DL-lactide-co-glycolide), a biocompatible, biodegradable polyester. The procedure used to prepare the microcapsules follows:

First, a polymer solution was prepared by dissolving 0.5 g of 50:50 poly(DL-lactide-co-glycolide) in 4.0 g of methylene chloride. Next, 300 microliters of an aqueous solution of TNP-KLH (46 mg TNP-LKH/mL; after dialysis) was added to and homogeneously dispersed in the poly(DL-lactide-co-glycolide) solution by vortexing the mixture with a Vortex-Genie 2 (Scientific Industries, Inc., Bohemia, N.Y.).

In a separate container, an 8 wt % aqueous PVA solution was prepared by dissolving 4.8 g of PVA in 55.2 g of deionized water. After dissolution of the PVA, the PVA solution was added to a 100-mL resin kettle (Kontes Glass, Inc., Vineland, N.J.) fitted with a truebore stirrer and a 1.5-in. TEFLON turbine impeller. The polymer solution was then added to the PVA processing medium by pouring through a long-stem 7-mm bore funnel. During this addition, the PVA solution was being stirred at about 650 rpm. After the resulting oil-in-water emulsion was stirred in the resin kettle for about 10 minutes, the contents of the resin kettle were transferred to 3.5 L of deionized water contained in a 4-L beaker and being stirred at about 800 rpm with a 2-in. stainless steel impeller. The resultant microcapsules were stirred in the deionized water for about 30 minutes, collected by centrifugation, washed twice with deionized water to remove any residual PVA, and were then collected by freeze drying. The microcapsule products consisted of spherical particles about 1 to 10 micrometers in diameter. Other microcapsules, such as staphylococcal enterotoxin B microcapsules, can be made in a similar manner.

The TNP-KLH content of the antigen-loaded microcapsules, that is, the core loading of the microcapsules, was determined by weighing out 10 mg of antigen-loaded microcapsules in a 12-mL centrifuge tube. Add 3.0 mL of methylene chloride to the tube and vortex to dissolve the poly(DL-lactide-co-glycolide). Next, add 3.0 mL of deionized water to the tube and vortex vigorously for 1 minute. Centrifuge the contents of the centrifuge tube to separate the organic and aqueous layers. Transfer the aqueous layer to a 10-mL volumetric flask. Repeat the extraction combining the aqueous layers in the volumetric flask. Fill the flask to the mark with deionized water. The amount of TNP-KLH in the flask, and subsequently the amount of TNP-KLH in the microcapsules, is then quantified using a protein assay. The microcapsules contained 0.2% TNP-KLH by weight. The staphylococcal enterotoxin B content of staphylococcal enterotoxin B microcapsules can be quantified in a similar manner.

II. PENETRATION OF DYE-LOADED MICROCAPSULES INTO THE PEYER'S PATCHES AFTER ORAL ADMINISTRATION

By far the largest mass of tissue with the capacity to function as an inductive site for secretory IgA responses is the Peyer's patches. These discrete nodules of lymphoreticular tissue are located along the entire length of the small intestine and appendix. The targeted delivery of intact antigen directly into this tissue to achieve high local concentration is currently believed to be the most effective means of inducing a disseminated mucosal IgA response. Biodegradable microcapsules represent an ideal vehicle to achieve this targeted vaccination.

EXAMPLE 1

Polystyrene Microcapsules

The uptake of microcapsules into the gut-associated lymphoreticular tissues and the size restriction of this penetration was investigated by orally administering to mice polystyrene microcapsules, loaded with the fluorescent dye coumarin. Unanesthetized, fasted BALB/c mice were administered 0.5 mL of a 100 mg/mL suspension of various sized fluorescent microcapsules (less than 5 micrometers or 8 to 50 micrometers in diameter) in tap water into the stomach using a feeding needle. At various times after administration (0.5, 1 and 2 hours), the mice were sacrificed and the small intestine excised. One-centimeter sections of gut containing a discrete Peyer's patch were isolated, flushed of lumenal contents, everted and snap frozen. Frozen sections were prepared and examined under a fluorescence microscope to observe the number, location and size of the microcapsules which were taken up into the Peyer's patch from the gut lumen.

Although some trapping of the microcapsules between the villi had prevented their removal during flushing, no penetration into the tissues was observed at any point except the Peyer's patch. At 0.5 hours after oral administration, microcapsules were observed in the Peyer's patch of the proximal, but not the distal, portion of the small intestine., With increasing time the microcapsules were transported by peristaltic movement such that by 2 hours they were throughout the gastrointestinal tract and could be found in the Peyer's patch of the ilium. The endocytosed microcapsules were predominantly located peripherally, away from the apex of the Peyer's patch dome, giving the impression that physical trapping between the dome and adjacent villi during peristalsis had aided in their uptake. Comparison of the efficiency of uptake of the <5 micrometer versus the 8 to 50 micrometer preparations demonstrated that microcapsules >10 micrometers in diameter were not absorbed into the Peyer's patches while microcapsules of 1 to 10 micrometers in diameter were rapidly and selectively taken up. This suggested that microcapsules composed of biodegradable wall materials would serve as an effective means for the targeted delivery of antigens to the lymphoreticular tissues for the induction of immunity at mucosal surfaces.

EXAMPLE 2

85:15 Poly(DL-lactide-co-glycolide) Microcapsules

1. Uptake of Biocompatible and Biodegradable Microcapsules into the Peyer's Patches Groups of mice were administered biodegradable microcapsules containing the fluorescent dye coumarin-6 as a suspension in tap water via a gastric tube. The microcapsule wall material chosen for these studies consisted of 85:15 poly(DL-lactide-co-glycolide) due to its ability to resist significant bioerosion for a period of six weeks. At various times from 1 to 35 days after administration, three representative Peyer's patches, the major mesenteric lymph nodes and the spleens from individual mice were removed, processed and serial frozen sections prepared.

When viewed with a fluorescence microscope using appropriate excitation and barrier filters the coumarin exhibited a deep green fluorescence which allowed the visual detection of microcapsules substantially less than 1 micrometer in diameter. All sections were viewed in order that the total number of microcapsules within each tissue or organ could be quantified. The size of each internalized microcapsule was determined using a calibrated eyepiece micrometer and its location within the tissue or organ was noted.

Internalized microcapsules of various sizes were observed in the Peyer's patches at 24 hours post oral administration and at all time points tested out to 35 days, as shown in Table 1. At no time were microcapsules of any size observed to penetrate into the tissue of the gut at any point other than the Peyer's patches. The total number of microcapsules within the Peyer's patches increased through Day 4 and then decreased over the following 31 days to approximately 15% of the peak number.

This is consistent with the observation that free microcapsules could be observed on the surface of the gut villi at the 1, 2 and 4 day time points. It is of interest that approximately 10 hours following oral administration of the microcapsule suspension the coumarin-loaded microcapsules were frankly observable in the passed feces. This clearance was followed with the aid of an ultraviolet light source and by 24 hours the vast majority of the ingested microcapsules had been passed. Thus, the continued uptake of microcapsules into the Peyer's patches observed at 2 and 4 days must be attributed to the minor fraction of the input dose which became entrapped within mucus between the gut villi. In addition, the efficiency of uptake for the entrapped microcapsules must be several orders of magnitude greater than that of the microcapsules present in the gut lumen, but above the mucus layer. These observations are important when these data are extrapolated to man; the tremendously larger mass of Peyer's patch tissue and the greatly increased transit time for the passage of material through the human small intestine relative to the mouse suggests that the efficiency of microcapsule uptake into the human Peyer's patches will be much higher.

Microcapsules of various sizes were observed within the Peyer's patches at all time points tested as shown in Table 1. At the 1, 2 and 4 day time points the proportion of <2 micrometers (45–47%), 2–5 micrometers (31–35%) and >5 micrometers (18–23%) microcapsules remained relatively constant. Evident at 7 days, and even more so at later time points, was a shift in the size distribution such that the small (<2 micrometers) and medium (2–5 micrometers) microcapsules ceased to predominate and the large (>5 micrometers) microcapsules became the numerically greatest species observed. This shift was concurrent with the decrease in total microcapsule numbers in the Peyer's patches observed on and after Day 7. These results are consistent with the preferential migration of the small and medium sizes of microcapsules from the Peyer's patches while the large (>5 micrometers) microcapsules are preferentially retained.

Consistent with the preferential migration of the small and medium microcapsules out of the Peyer's patches are the data pertaining to the location of microcapsules within the architecture of the Peyer's patches. When a microcapsule was observed within the Peyer's patch, it was noted to be either relatively close to the dome epithelium where it entered the Peyer's patch (within 200 micrometers) or deeper within the lymphoid tissue ($\geq 200$ micrometers from the closest identifiable dome epithelium) (Table 1). Microcapsules observed deep within the Peyer's patch tissue were almost exclusively of small and medium diameter. At 1 day post-administration, 92% of the microcapsules were located close to the dome epithelium. The proportion of deeply located microcapsules increased through Day 4 to 24% of the total, and thereafter decreased with time to approximately 2% at Day 14 and later. Thus, the small and medium microcapsules migrate through and out of the Peyer's patches, while the large (>5 micrometers) microcapsules remain within the dome region for an extended period of time.

2. Microcapsule Migration to the Mesenteric Lymph Nodes and Spleen

A small number of microcapsules were observed in the mesenteric lymph nodes at 1 day post-administration, and the numbers, progressively increased through Day 7, as shown in Table 2. After Day 7, the numbers decreased but were still detectable on Day 35. The size distribution clearly showed that microcapsules >5 micrometers in diameter did not enter this tissue, and the higher proportion of small (<2 micrometers) relative to medium (2–5 micrometers) microcapsules at the earlier time points indicated that the smaller diameter microcapsules migrate to this tissue with greatest efficiency. In addition, at the earlier time points, the majority of the microcapsules were located just under the capsule in the subcapsular sinus. Later time points showed a shift in the distribution to deep within the lymph node structure, and by day 14, 90% of the microcapsules were located within the cortex and medullary regions. The observation that the microcapsules are first detected in or near the subcapsular sinus is consistent with their entry into this tissue via the lymphatics which drain the Peyer's patches. A progressive increase in the proportion of the microcapsules located deep in this tissue, clearly discernable at Day 4, followed by a progressive drop in the total numbers on Day 14 and later, suggests that the microcapsules progress through this tissue and extravasate through the efferent lymphatic drainage.

Similar examination of the spleen showed that no microcapsules were detectable until Day 4 post-administration. Peak numbers of microcapsules were not observed in this organ until Day 14. As in the case of the mesenteric lymph nodes, no microcapsules of >5 micrometers in diameter were observed. At all time points, the microcapsules were observed deep in this organ within the cortex. It should be noted that the peak number of microcapsules was observed in the spleen at a time when the majority of the microcapsules present in the mesenteric lymph nodes was deeply located and their total numbers falling. These data are consistent with the known pattern of lymph drainage from the Peyer's patches to the mesenteric lymph nodes and from the mesenteric lymph nodes to the bloodstream via the thoracic duct. Thus, it appears that the microcapsules present in the spleen have traversed the Peyer's patches and mesenteric lymph nodes and have entered the spleen via the blood circulation.

In additional experiments, tissue sections from Peyer's patches, mesenteric lymph node and spleen which contained absorbed 85:15 DL-PLG microcapsules were examined by histochemical and immunohistochemical techniques. Among other observations, these studies clearly showed that the microcapsules which were absorbed into the Peyer's patches were present within macrophage-like cells which were stained by periodic acid Schiff's reagent (PAS) for intracellular carbohydrate, most probably glycogen, and for major histocompatibility complex (MHC) class II antigen. Further, the microcapsules observed in the mesenteric lymph nodes and in the spleen were universally found to have been carried there within these PAS and MHC class II positive cells. Thus, the antigen containing microcapsules have been internalized by antigen-presenting accessory cells (APC) in the Peyer's patches, and these APC have disseminated the antigen-microcapsules to other lymphoid tissues.

These data indicate that the quality of the immune response induced by orally administering a microencapsulated vaccine can be controlled by the size of the particles. Microcapsules <5 micrometers in diameter extravasate from the Peyer's patches within APC and release the antigen in lymphoid tissues which are inductive sites for systemic immune responses. In contrast, the microcapsules 5 to 10 micrometers in diameter remain in the Peyer's patches, also within APC, for extended time and release the antigen into this sIgA inductive site.

EXAMPLE 3
Comparison of the Uptake of Microcapsules of 10 Compositions by the Peyer's Patches Experiments were performed to identify microcapsule polymeric excipients that would be useful for a practical controlled release delivery system and which would possess the physicalchemical properties which would allow for targeted absorption of microcapsules into the mucosally-associated lymphoid tissues. In regard to the latter consideration, research has shown that hydrophobic particles are more readily phagocytized by the cells of the reticuloendothelial system. Therefore, the absorption into the Peyer's patches of 1- to 10-micrometer microcapsules of 10 different polymers which exhibit some range with respect to hydrophobicity was examined. The wall materials chosen for these studies consisted of polymers that varied in water uptake, biodegradation, and hydrophobicity. These polymers included polystyrene, poly(L-lactide), poly(DL-lactide), 50:50 poly(DL-lactide-co-glycolide), 85:15 poly(DL-lactide-co-glycolide), poly(hydroxybutyric acid), poly(methyl methacrylate), ethyl cellulose, cellulose acetate hydrogen phthalate, and cellulose triacetate. Microcapsules, prepared from 7 of the 10 excipients, were absorbed and were predominantly present in the dome region of the Peyer's patches 48 hours after oral administration of a suspension containing 20 mg of microcapsules, as shown in Table 3. None of the microspheres were seen to penetrate into tissues other than the Peyer's patches. With one exception, ethyl cellulose, the efficiency of absorption was found to correlate with the relative hydrophobicity of the excipient. Up to 1,500 microcapsules were observed in the 3 representative Peyer's patches of the mice administered the most hydrophobic group of compounds [poly(styrene), poly(methyl methacrylate), poly(hydroxybutyrate)], while 200 to 1,000 microcapsules were observed with the relatively less hydrophobic polyesters [poly(L-lactide), poly(DL-lactide), 85:15 poly(DL-lactide-co-glycolide), 50:50 poly(DL-lactide-co-glycolide)]. As a class, the cellulosics were not absorbed.

It has been found that the physicalchemical characteristics of the microcapsules regulate the targeting of the microcapsules through the efficiency of their absorption from the gut lumen by the Peyer's patches, and that this is a surface phenomenon. Therefore, alterations in the surface characteristics of the microcapsules, in the form of chemical modifications of the polymer or in the form of coatings, can be used to regulate the efficiency with which the microcapsules target the delivery of bioactive agents to mucosally-associated lymphoid tissues and to APC. Examples of coatings which may be employed but are not limited to, chemicals, polymers, antibodies, bioadhesives, proteins, peptides, carbohydrates, lectins and the like of both natural and man made origin.

III. ANTIBODY RESPONSES INDUCED WITH MICROENCAPSULATED VACCINES

MATERIALS AND METHOD

Mice, BALB/c mice, 8 to 12 weeks of age, were used in these studies.

Trinitrophenyl—Keyhole Limpet Hemocyanin

Hemocyanin from the keyhole limpet (KLH) Megathura crenulate was purchased from Calbiochem (San Diego, Calif.). It was conjugated with the trinitrophenyl hapten (TNP-KLH) using 2, 4, 6-trinitrobenzene sulfonic acid according to the procedure of Rittenburg and Amkraut (Rittenburg, M. B. and Amkraut, A. A. Immunogenicity of trinitrophenyl-hemocyanin: Production of primary and secondary anti-hapten precipitins. J. Immunol. 97:421; 1966). The substitution ratio was spectrophotometrically determined to be $TNP_{861}$-KLH using a molar extinction coefficient of 15,400 at a wavelength of 350 nm and applying a 30% correction for the contribution of KLH at this wavelength.

Staphylococcal Enterotoxin B Vaccine

A formalinized vaccine of staphylococcal enterotoxin B (SEB) was prepared as described by Warren et al. (Warren, J. R., Spero, L. and Metzger, J. F. Antigenicity of formalin-inactivated staphylococcal enterotoxin B. J. Immunol. 111:885; 1973). In brief, 1 gm of enterotoxin was dissolved in 0.1M sodium phosphate buffer, pH 7.5, to 2 mg/mL. Formaldehyde was added to the enterotoxin solution to achieve a formaldehyde:enterotoxin mole ratio of 4300:1. The solution was placed in a slowly shaking 37° C. controlled environment incubator-shaker and the pH was monitored and maintained at 7.5+0.1 daily. After 30 days, the toxoid was concentrated and washed into borate buffered saline (BBS) using a pressure filtration cell (Amicon), and sterilized by filtration. Conversion of the enterotoxin to enterotoxoid was confirmed by the absence of weight loss in 3 to 3.5 kg rabbits injected intramuscularly with 1 mg of toxoided material.

Immunizations

Microencapsulated and nonencapsulated antigens were suspended at an appropriate concentration in a solution of 8 parts filter sterilized tap water and 2 parts sodium bicarbonate (7.5% solution). The recipient mice were fasted overnight prior to the administration of 0.5 mL of suspension via gastric intubation carried out with an intubation needle (Babb, J. L., Kiyono, H., Michalek, S. M. and McGhee, J. R. LPS regulation of the immune response: Suppression of immune response to orally-administered T-dependent antigen. J. Immunol. 127:1052; 1981).

Collection of Biological Fluids

1. Plasma

Blood was collected in calibrated capillary pipettes following puncture of the retro-orbital plexus. Following clot formation, the serum was collected, centrifuged to remove red cells and platelets, heat-inactivated, and stored at −70° C. until assayed.

2. Intestinal Secretions

Mice were administered four doses (0.5 mL) of lavage solution [25 mM NaCl, 40 mM $Na_2SO_4$, 10 mM KCl, 20 mM NaHCO$_3$, and 48.5 mM poly(ethylene glycol), osmolarity of 530 mosM] at 15-minute intervals (Elson, C. O., Ealding, W. and Lefkowitz, J. A lavage technique allowing repeated measurement of IgA antibody on mouse intestinal secretions. J. Immunol. Meth. 67:101; 1984). Fifteen minutes after the last dose of lavage solution, the mice were anesthetized and after an additional 15 minutes they were administered 0.1 mg pilocarpine by ip injection. Over the next 10 to 20 minutes, a discharge of intestinal contents was stimulated. This was collected into a petri dish containing 3 mL of a solution of 0.1 mg/mL soybean trypsin inhibitor (Sigma, St. Louis, Mo.) in 50 mM EDTA, vortexed vigorously and centrifuged to remove suspended matter. The supernatant was transferred to a round-bottom, polycarbonate centrifuge tube and 30 microliters of 20 millimolar phenylmethylsulfonyl fluoride (PMSF, Sigma) was added prior to clarification by high-speed centrifugation (27,000× g, 20 minutes, 4° C.). After clarification, 20 microliters each of PMSF and 1% sodium azide were added and the solution made 10% in FCS to provide an alternate substrate for any remaining proteases.

3. Saliva

Concurrent with the intestinal discharge, a large volume of saliva is secreted and 0.25 mL was collected into a pasteur pipette by capillary action. Twenty microliters each of trypsin inhibitor, PMSF, sodium azide and FCS was added prior to clarification.

4. Bronchial-Alveolar Wash Fluids

Bronchial-alveolar wash fluids were obtained by lavaging the lungs with 1.0 mL of PBS. An animal feeding needle was inserted intratracheally and fixed in place by tying with suture material. The PBS was inserted and withdrawn 5 times to obtain washings, to which were added 20 microliters each of trypsin inhibitor, PMSF, sodium azide, and FCS prior to clarification by centrifugation.

5. Immunochemical Reagents

Solid-phase absorbed and affinity-purified polyclonal goat IgG antibodies specific for murine IgM, IgG and IgA were obtained commercially (Southern Biotechnology Associates, Birmingham, Ala.). Their specificity in radioimmunoassays was tested through their ability to bind appropriate purified monoclonal antibodies and myeloma proteins.

6. Solid-Phase Radioimmunoassays

Purified antibodies were labeled with carrier-free Na $^{125}$I (Amersham) using the chloramine T method [Hunter, W. M. Radioimmunoassay. In: Handbook of Experimental Immunology, M. Weir (editor). Blackwell Scientific Publishing, Oxford, p. 14.1; 1978). Immulon Removawell assay strips (Dynatech) were coated with TNP conjugated bovine serum albumin (BSA) or staphylococcal enterotoxin B at 1 microgram/mL in BBS overnight at 4° C. Control strips were left uncoated but all strips were blocked for 2 hours at room temperature with 1% BSA in BBS, which was used as the diluent for all samples and $^{125}$I-labeled reagents. Samples of biologic fluids were appropriately diluted, added to washed triplicate replicate wells, and incubated 6 hours at room temperature. After washing, 100,000 cpm of $^{125}$I-labeled isotype-specific anti-immunoglobulin was added to each well and incubated overnight at 4° C. Following the removal of unbound $^{125}$I-antibodies by washing, the wells were counted in a Gamma 5500 spectrometer (Beckman Instruments, Inc., San Ramon, Calif.). In the case of the assays for TNP specific antibodies, calibrations were made using serial twofold dilutions of a standard serum (Miles Scientific, Naperville, Ill.) containing known amounts of immunoglobulins, on wells coated with 1 microgram/well isotype-specific antibodies. Calibration curves and interpolation of unknowns was obtained by computer, using "Logit-log" or "Four Parameter Logistic" BASIC Technology Center (Vanderbilt Medical Center, Nashville, Tenn.). In the case of antibodies specific to staphylococcal enterotoxin B, the results are presented as the reciprocal serum dilution producing a signal >3-fold that of the group-matched prebleed at the same dilution (end-point titration).

A. Vaccine-Microcapsules Administered by Injection

1. Adjuvant Effect Imparted by Microencapsulation

EXAMPLE 1

Adjuvant Effect Imparted by Microencapsulation-Intraperitoneal Administration

Research in our laboratories has shown that microencapsulation results in a profoundly heightened immune response to the incorporated antigen or vaccine in numerous experimental systems. An example is provided by the direct comparison of the level and isotype distribution of the circulating antibody response to Staphylococcal enterotoxin B, the causative agent of Staphylococcal food poisoning, following immunization with either soluble or microencapsulated enterotoxoid. Groups of mice were administered various doses of the toxoid vaccine incorporated in 50:50 poly(DL-lactide-co-glycolide) microcapsules, or in soluble form, by intraperitoneal (IP) injection. On Days 10 and 20 following immunization, plasma samples were obtained and assayed for anti-toxin activity by end-point titration in isotype-specific immunoradiometric assays (Table 4). The optimal dose of soluble toxoid (25 micrograms) elicited a characteristically poor immune response to the toxin which was detected only in the IgM isotype. In contrast, the administration of 25 micrograms of toxoid incorporated within microcapsules induced not only an IgM response, but an IgG response which was detectable at a plasma dilution of ½,560 on Day 20 post immunization. In addition, larger doses of toxoid could be administered in microencapsulated form without decreasing the magnitude of the response, as is seen with the 50 microgram dose of soluble toxoid. In fact, the measured release achieved with the microcapsules allows for 4–5 times the dose to be administered without causing high zone paralysis, resulting in substantially heightened immunity. This adjuvant activity is even more pronounced following secondary (Table 5) and tertiary immunizations (Table 6).

The Day 20 IgG anti-toxin response following secondary immunization was 512 times higher in mice receiving 50 micrograms of microencapsulated toxoid than in mice receiving the optimal dose of soluble toxoid. Further, tertiary immunization with the soluble toxoid at its optimal dose was required to raise an antibody response to the toxin which was equivalent to that observed following a single immunization with 100 micrograms of microencapsulated enterotoxoid. Adjuvant activity of equal magnitude has been documented to common laboratory protein antigens such as haptenated keyhole limpet hemocyanin and influenza virus vaccine.

EXAMPLE 2

Adjuvant Effect Imparted by Microencapsulation-Subcutaneous Administration.

The present delivery system was found to be active following intramuscular or subcutaneous (SC) injection. This was investigated by directly comparing the time course and level of the immune response following IP and SC injection into groups of mice, as shown in Table 7.

One hundred micrograms of enterotoxoid in microspheres administered by SC injection at 4 sites along the backs of mice stimulated a peak IgG anti-toxin response equivalent to that observed following IP injection. Some delay in the kinetics of anti-toxin appearance were observed. However, excellent antibody levels were attained, demonstrating the utility of injection at sites other than the peritoneum. Following secondary immunization the IP and SC routes were again equivalent with respect to peak titer, although the delayed response of the SC route was again evident, as shown in Table 8.

2. Mechanism of the Adjuvant Effect Imparted by Microencapsulation.

EXAMPLE 1

The Adjuvant Effect Imparted by Microencapsulation is Not the Result of Adjuvant Activity Intrinsic to the Polymer When considering the mechanism through which 1–10 micrometer DL-PLG microspheres mediate a potentiated humoral immune response to the encapsulated antigen, three mechanisms must be considered as possibilities. First, the long term chronic release (depot), as compared to a bolus dose of nonencapsulated antigen, may play a role in immune enhancement. Second, our experiments have shown that microspheres in this size range are readily phagocytized by antigen processing and presenting cells. Therefore, targeted delivery of a comparatively large dose of nondegraded antigen directly to the cells responsible for the initiation of immune responses to T cell-dependent antigens must also be considered. Third, the microcapsules may possess intrinsic immunopotentiating activity through their ability to activate cells of the immune system in a manner analogous to adjuvants such as bacterial lipopolysaccharide or muramyl-di-peptide. Immunopotentiation by this latter mechanism has the characteristic that it is expressed when the adjuvant is administered concurrently with the antigen.

In order to test whether microspheres possess any innate adjuvancy which is mediated through the ability of these particles to nonspecifically activate the immune system, the antibody response to 100 micrograms of microencapsulated enterotoxoid was compared to that induced following the administration of an equal dose of enterotoxoid mixed with placebo microspheres containing no antigen. The various antigen forms were administered by IP injections into groups of 10 BALB/c mice and the plasma IgM and IgG enterotoxin-specific antibody responses determined by endpoint titration RIAs, as shown in Table 9.

The plasma antibody response to a bolus injection of the optimal dose of soluble enterotoxoid (25 micrograms) was characteristically poor and consisted of a peak IgM titer of 800 on day 10 and a peak IgG titer of 800 on day 20. Administration of an equal dose of microencapsulated enterotoxoid induced a strong response in both the IgM and IgG isotypes which was still increasing on day 30 after immunization. Co-administration of soluble enterotoxoid and a dose of placebo microspheres equal in weight, size and composition to those used to administer encapsulated antigen did not induce a plasma anti-toxin response which was significantly higher than that induced by soluble antigen alone. This result was not changed by the administration of the soluble antigen 1 day before or 1, 2 or 5 days after the placebo microspheres. Thus, these data indicate that the immunopotentiation expressed when antigen is administered within 1–10 micrometer DL-PLG microspheres is not a function of the ability of the microspheres to intrinsically activate the immune system. Rather, the data are consistent with either a depot effect, targeted delivery of the antigen to antigen-presenting accessory cells, or a combination of these two mechanisms.

EXAMPLE 2

Retarding the Antigen-Release Rate from 1–10 Micrometer Microcapsules Increases the Level of the Antibody Response and Delays the the Time of the Peak Response Four enterotoxoid containing microcapsule preparations with a variety of antigen release rates were compared for their ability to induce a plasma anti-toxin response following IP injection. The rate of antigen release by the microcapsules used in this study is a function of two mechanisms; diffusion through pores in the wall matrix and hydrolysis (bioerosion) of the wall matrix. Batches #605-026-1 and #514-140-1 have varying initial rates of release through pores, followed by a second stage of release which is a function of their degradation through hydrolysis. In contrast, Batches #697-143-2 and #928-060-00 have been manufactured with a tight uniform matrix of wall material which has little release through pores and their release is essentially a function of the rate at which the wall materials are hydrolyzed. However, these latter two lots differ in the ratio of lactide to glycolide composing the microcapsules, and the greater resistance of the 85:15 DL-PLG to hydrolysis results in a slower rate of enterotoxoid release.

The immune response induced by Batch #605-026-1 (60% release at 48 hours) reached a peak IgG titer of 6,400 on day 20 (Table 10). Batch #514-140-1 (30% release at 48 hours) stimulated IgG antibodies which also peaked on day 20, but which were present in higher concentration both on days 20 and 30.

Immunization with Batch #697-143-2 (10% release at 48 hours) resulted in peak IgG antibody levels on days 30 and 45 which were substantially higher (102,400) than those induced by either lot with early release. Further delaying the rate of antigen release through the use of an 85:15 ratio of lactide to glycolide, Batch #928-060-00 (0% release at 48 hours) delayed the peak antibody levels until days 45 and 60, but no further increase in immunopotentiation was observed.

These results are consistent with a delayed and sustained release of antigen stimulating a higher antibody response. However, certain aspects of the pattern of responses induced by these various microspheres indicate that a depot effect is not the only mechanism of immunopotentiation. The faster the initial release, the lower the peak antibody titer. These results are consistent with a model in which the antigen released within the first 48 hours via diffusion through pores is no more effective than the administration of soluble antigen. Significant delay in the onset of release to allow time for phagocytosis of the microspheres by macrophages allows for the effective processing and presentation of the antigen, and the height of the resulting response is governed by the amount of antigen delivered into the presenting cells. However, delay of antigen release beyond the point where all the antigen is delivered into the presenting cells does not result in further potentiation of the response, it only delays the peak level.

EXAMPLE 3

Correlation of the Size of the Microcapsules with the Resultant Adjuvant Effect

It has been consistently observed that the size of the microspheres has a profound effect on the degree to which the antibody response is potentiated and the time at which it is initiated. These effects are best illustrated under conditions of a limiting antigen dose. Mice immunized subcutaneously with 10 $\mu$g of SEB toxoid encapsulated in 1–10 $\mu$m microspheres produced a more rapid, and a substantially more vigorous, IgG anti-toxin response than did mice immunized with the same dose of toxoid in 10–110 $\mu$m microspheres as shown in FIG. 1. Groups of 5 mice were subcutaneously immunized with 10 $\mu$g of SEB toxoid encapsulated in 1–10 $\mu$m (85:15 DL-PLG; 0.065 wt % SEB toxoid) or 10–110 $\mu$m (85:15 DL-PLG; 1.03 wt % SEB toxoid) microspheres. Plasma samples were obtained at 10 day intervals and the IgG anti-toxin titer determined by end-point titration in a RIA using solid-phase adsorbed SEB toxin.

A likely explanation for these effects involves the manner in which these different sizes of microspheres deliver antigen into the draining lymphatics. We have observed fluorescent DL-PLG microspheres of <10 μm in diameter to be efficiently phagocytized and transported by macrophages into the draining lymph nodes. In contrast, larger microspheres (>10 μm) remain localized at the site of injection. Taken together, these data suggest that the extremely strong adjuvant activity of <10 μm microspheres is due to their efficient loading of antigen into accessory cells which direct the delivery of the microencapsulated antigen into the draining lymph nodes.

3. Pulsatile Release of Vaccines from Microcapsules for Programmed Boosting Following a Single Injection When one receives any of a number of vaccines by injection, two to three or more administrations of the vaccine are required to illicit a good immune response. Typically, the first injection is given to afford a primary response, the second injection is given to afford a secondary response, and a third injection is given to afford a tertiary response. Multiple injections are needed because repeated interaction of the antigen with immune system cells is required to stimulate a strong immunological response. After receiving the first injection of vaccine, a patient, therefore, must return to the physician on several occasions to receive the second, third, and subsequent injections to acquire protection. Often patients never return to the physician to get the subsequent injections.

The vaccine formulation that is injected into a patient may consist of an antigen in association with an adjuvant. For instance, an antigen can be bound to alum. During the first injection, the use of the antigen/adjuvant combination is important in that the adjuvant aids in the stimulation of an immune response. During the second and third injections, the administration of the antigen improves the immune response of the body to the antigen. The second and third administrations or subsequent administrations, however, do not necessarily require an adjuvant.

Alza Corporation has described methods for the continuous release of an antigen and an immunopotentiator (adjuvant) to stimulate an immune response (U.S. Pat. No. 4,455,142). This invention differs from the Alza patent in at least two important manners. First, no immunopotentiator is required to increase the immune response, and second, the antigen is not continuously released from the delivery system.

The present invention concerns the formulation of vaccine (antigen) into microcapsules (or microspheres) whereby the antigen is encapsulated in biodegradable polymers, such as poly(DL-lactide-co-glycolide). More specifically, different vaccine microcapsules are fabricated and then mixed together such that a single injection of the vaccine capsule mixture improves the primary immune response and then delivers antigen in a pulsatile fashion at later time points to afford secondary, tertiary, and subsequent responses.

The mixture of microcapsules may consist of small and large microcapsules. The small microcapsules, less than 10 microns, preferably less than 5 micrometers, or more preferable 1 to 5 micrometers, potentiate the primary response (without the need of an adjuvant) because the small microcapsules are efficiently recognized and taken up by macrophages. The microcapsules inside of the macrophages then release the antigen which is subsequently processed and presented on the surface of the macrophage to give the primary response. The larger microcapsules, greater than 5 micrometers, preferably greater than 10 microns, but not so large that they cannot be administered for instance by injection, preferably less than 250 micrometers, are made with different polymers so that as they biodegrade at different rates, they release antigen in a pulsatile fashion.

Furthermore, the mixture of microcapsules may consist entirely of microcapsules sized less than 10 micrometers. Microspheres less than 10 micrometers in diameter are rapidly phagocytized by macrophages after administration. By using mixtures of microspheres less than 10 micrometers in diameter that have been prepared with polymers that have various lactide/glycolide ratios, an immediate primary immunization as well as one or more discrete booster immunizations at the desired intervals (up to approximately eight months after administration) can be obtained. By mixing microspheres less than 10 micrometers in diameter (for the primary immunization) with microspheres greater than 10 micrometers in diameter, the time course possible for delivery of the discrete booster immunizations can be extended up to approximately 2 years. This longer time course is possible because the larger microspheres are not phagocytized and are therefore degraded at a slower rate than are the less than 10 micrometer microspheres.

Using the present invention, the composition of the antigen microcapsules for the primary response is basically the same as the composition of the antigen microcapsules used for the secondary, tertiary, and subsequent responses. That is, the antigen is encapsulated with the same class of biodegradable polymers. The size and pulsatile release properties of the antigen microcapsules then maximizes the immune response to the antigen.

The preferred biodegradable polymers are those whose biodegradation rates can be varied merely by altering their monomer ratio, for example, poly(DL-lactide-co-glycolide), so that antigen microcapsules used for the primary response will biodegrade faster than antigen microcapsules used for subsequent responses, affording pulsatile release of the antigen.

In summary, by controlling the size of the microcapsules of basically the same composition, one can maximize the immune response to an antigen. Also important is having small microcapsules (microcapsules less than 10 micrometers, preferably less than 5 micrometers, most preferably 1 to 5 micrometers) in the mixture of antigen microcapsules to maximize the primary response. The use of an immune enhancing delivery system, such as small microcapsules, becomes even more important when one attempts to illicit an immune response to less immunogenic compounds such as killed vaccines, subunit vaccines, low-molecular-weight vaccines such as peptides, and the like.

EXAMPLE 1
Co-administration of Free and Microencapsulated Vaccine.

A Japanese Encephalitis virus vaccine (Biken) was studied. The virus used is a product of the Research Foundation for Microbial Disease of Osaka University, Suita, Osaka, Japan. The manufacturer recommends a three dose immunization series consisting of two doses of vaccine administered one to two weeks apart followed by administration of a third dose of vaccine one month after the initial immunization series. We have compared the antiviral immune responses of mice immunized with a standard three dose schedule of JE vaccine to the antiviral response of mice immunized with a single administration of JE vaccine consisting of one part unencapsulated vaccine and two parts encapsulated vaccine. The JE microcapsules were >10 micrometers. The results of immunizing mice with JE vaccine by these two methods were compared by measuring the serum antibody titers against JE vaccine detected through an ELISA assay. The ELISA assay measures the presence of serum antibodies with specificity of JE vaccine components, however, it does not measure the level of virus neutralizing antibody present in the serum. The virus neutralizing antibody activity was therefore measured by virus cytopathic effect (CPE) inhibition assays and virus plaque reduction assays. The results of those assays are presented here.

Four experimental groups consisting of (1) untreated control mice which receive no immunization; (2) mice which received 3.0 mg of JE vaccine (unencapsulated) on Day 0; (3) mice which received 3.0 mg of JE vaccine (unencapsulated) on Days 0, 14 and 42 (standard schedule) and (4) mice which received 3.0 mg of JE vaccine (unencapsulated) and 3.0 mg of JE vaccine (encapsulated) on day 0 were studied. The untreated controls provide background virus neutralization titers against which immunized animals can be compared. The animals receiving a single 3.0 mg dose of JE vaccine on Day 0 provide background neutralization titers against which animals receiving unencapsulated vaccine in conjunction with encapsulated vaccine can be compared. This comparison provides evidence that the administration of encapsulated vaccine augments the immunization potential of a single 3.0 mg dose of unencapsulated vaccine. The animals receiving 3 doses of unencapsulated vaccine provide controls against which the encapsulated vaccine group can be compared so as to document the ability of a single injection consisting of both nonencapsulated and encapsulated vaccine to produce antiviral activity comparable to a standard three dose immunization schedule.

Serum samples collected on Days 21, 49 and 77 from ten animals in each experimental group were tested for their ability to inhibit the cytopathic effects induced by a standard challenge (100 $TCID_{50}$) of JE virus. The results of the CPE inhibition assays, expressed as the highest serum dilution capable of inhibiting 50% of the viral CPE, are presented in Table 11. As is shown, the untreated control animals (Group 1) had no significant serum virus neutralizing activity at any point tested. Of the ten animals receiving a single 3.0 mg dose of JE vaccine on Day 0 (Group 2), one did not develop any detectable virus neutralizing antibody. Of the remaining nine mice, the highest titer achieved was 254 which occurred on Day 49. The geometric mean antiviral titer for this experimental group peaked on Day 49. Of the ten animals receiving a standard schedule of three vaccine doses (Group 3), eight had a decrease in antibody activity from Day 49 to Day 77. The geometric mean titer for this group decreased by greater than 50% from Day 40 to Day 77. All ten animals receiving encapsulated JE vaccine (Group 4) developed serum antiviral activity. The geometric mean titer for this group increased from Day 21 to Day 77. The average titer occurring on Day 49 in this group was significantly lower than that occurring in the 3 vaccine dose group (Group 3) (p=0.006); however, the titer continued to increase from Day 49 to Day 77 which is in contrast to the 3 vaccine dose group. There was no significant difference in the average titer for these two groups in the Day 77 samples (p=0.75) indicating that the encapsulated vaccine group achieved comparable serum antiviral titers at Day 77. Unlike the 3 vaccine dose group (Group 3), the animals receiving encapsulated vaccine (Group 4) continued to demonstrate increases in serum virus neutralizing activity throughout the timepoints examined. In contrast to the standard vaccine treatment group, mice receiving encapsulated JE vaccine had a two-fold increase in the average serum neutralizing titer from Day 49 to Day 77. The Day 21 average antiviral titer from mice receiving microencapsulated vaccine was not significantly different from the Day 21 average titer of mice receiving a single dose of JE vaccine on Day 0 (p=0.12); however, the day 49 and Day 77 average titers were significantly different for the two groups (p=0.03 and p=0.03, respectively). These data indicate that serum virus neutralizing titers similar to those produced by standard vaccine administration can be achieved by administering a single dose of encapsulated JE vaccine. Although the antiviral titers achieved with the excipient formulation used in this study did not increase as rapidly as those achieved with the standard vaccine, the serum neutralizing antibody activity did reach titers which are comparable to those achieved with the standard three dose vaccine schedule.

To further corroborate these findings, pooled samples produced by mixing equal volumes of each serum sample were prepared for each experimental group. These samples were submitted to an independent laboratory for determination of antiviral activity. The samples were tested by plaque reduction assay against a standard challenge of JE virus. The results of these assays, presented in Table 12, substantiate the findings described above. Although the animals receiving encapsulated vaccine did not reach peak titers as rapidly as did the standard vaccine group, the encapsulated vaccine did induce comparable virus neutralizing antibody activity. Furthermore, the encapsulated vaccine maintained a higher antiviral titer over a longer period of time than did the standard vaccine. These results further support the conclusion that a single administration of microencapsulated vaccine can produce results comparable to those achieved with a three dose schedule of standard vaccine.

EXAMPLE 2

Co-administration of <10 Micrometer Priming and >10 Micrometer Pulsing Vaccine Microcapsules One advantage of the copolymer microcapsule delivery system is the ability to control the time and/or rate at which the incorporated material is released. In the case of vaccines this allows for scheduling of the antigen release in such a manner as to maximize the antibody response following a single administration. Among the possible release profiles which would be expected to improve the antibody response to a vaccine is a pulsed release (analogous to conventional booster immunizations).

The possibility of using size as a mechanism to control vaccine release is based on the observation that microspheres <10 micrometers in diameter are phagocytized by macrophages and release antigen at a substantially accelerated rate relative to microspheres made of the same DL-PLG but which are too large to be phagocytized. The possibility of using size to achieve pulsed vaccine release was investigated by systemically (subcutaneously) injecting 100 micrograms of enterotoxoid to groups of mice either in 1–10 micrometer (50:50 DL-PLG; 1.51 wt % enterotoxoid), 20–50 micrometers (50:50 DL-PLG; 0.64 wt % enterotoxoid) or in a mixture of 1–10 micrometer and 20–50 micrometer microcapsules in which equal parts of the enterotoxoid were contained within each size range. The groups of mice were bled at 10 day intervals and the plasma IgG responses were determined by endpoint titration in isotype-specific immunoradiometric assays employing solid-phase absorbed enterotoxin (FIG. 2). Following the administration of the 1–10 micrometer enterotoxoid microcapsules the plasma IgG response was detected on day 10, rose to a maximal titer of 102,400 on days 30 and 40, and decreased through day 60 to 25,600. In contrast, the response to the toxoid administered in 20–50 micrometer microcapsules was delayed until day 30, and thereafter increased to a titer of 51,200 on days 50 and 60. The concomitant administration of equal parts of the toxoid in 1–10 and 20–50 micrometer microcapsules produced an IgG response which was for the first 30 days essentially the same as that stimulated by the 1–10 micrometer microcapsules administered alone. However, beginning on day 40 the response measured in the mice concurrently receiving the 1–10 plus 20–50 micrometer microcapsules steadily increased to a titer of 819,200 on day 60, a level which was far more than the additive amount of the responses induced by the two size ranges administered singly.

The antibody response obtained through the co-administration of 1–10 and 20–50 micrometer enterotoxoid-containing microcapsules is consistent with a two phase (pulsed) release of the antigen. The first pulse results from the rapid ingestion and accelerated degradation of the 1–10 micrometer particles by tissue histiocytes, which results in a potentiated primary immune response due to the efficient loading of high concentrations of the antigen into these accessory cells, and most probably their activation. The second phase of antigen release is due to the biodegradation of the 20–50 micrometer microcapsules, which are too large to be ingested by phagocytic cells. This second pulse of antigen is released into a primed host and stimulates an anamnestic immune response. Thus, using the 50:50 DL-PLG copolymer, a single injection vaccine delivery system can be constructed which potentiates antibody responses (1–10 micrometer microcapsules), and which can deliver a timed and long lasting secondary booster immunization (20–50 micrometer microcapsules). In addition, through alteration of the ratio of the copolymers, it is possible to prepare formulations which release even later, in order to provide tertiary or even quaternary boostings without the need for additional injections.

EXAMPLE 3

Figure 3:
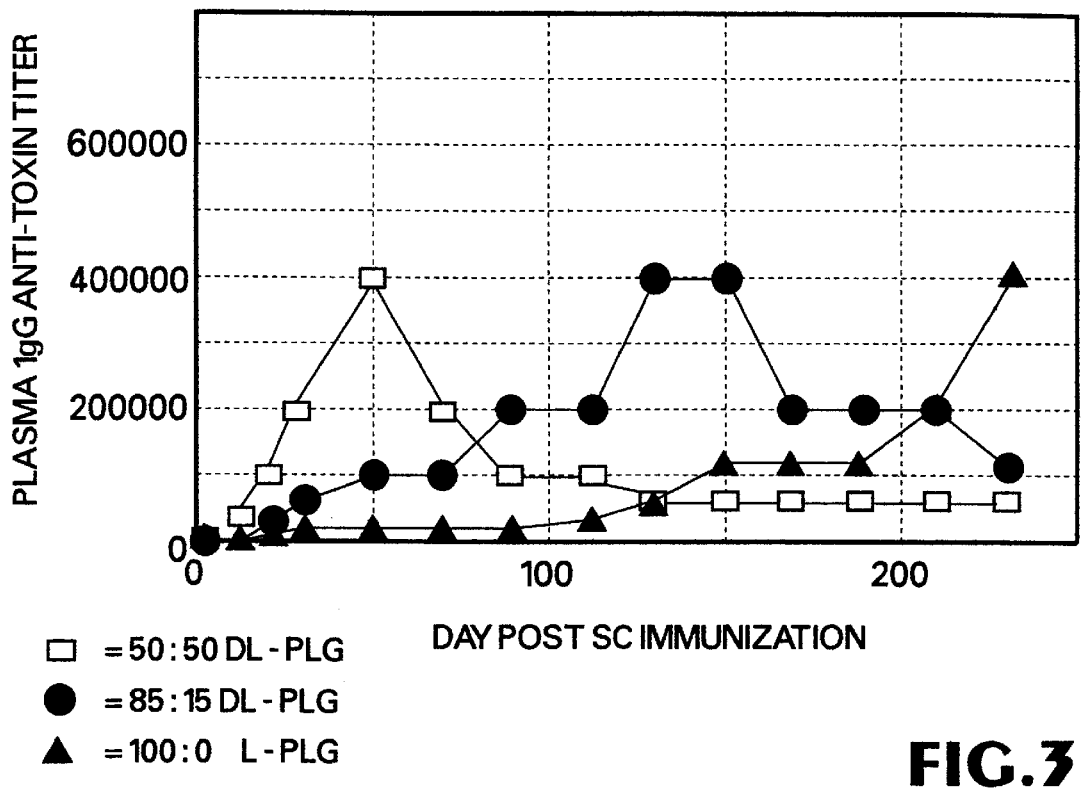
FIG. 3 represents the plasma IgG responses in mice following subcutaneous administration of 1–10 $\mu$m 50:50 DL-PLG, 85:15 DL-PLG, and 100:0 L-PLG SEB toxoid-containing microcapsules.

Co-administration of <10 Micrometer Priming and <10 Micrometer Pulsing Vaccine Microcapsules The hydrolysis rate of the DL-PLG copolymer can be changed by altering the lactide-to-glycolide ratio. This approach to the pulsed release of vaccine antigens was investigated in experiments in which groups of mice were subcutaneously immunized with 10 $\mu$g of SEB toxoid in 1 to 10 micrometer microspheres formulated from DL-PLG with lactide-to-glycolide ratios of 50:50 or 85:15 DL-PLG or 100:0 L-PLG. Determination of the plasma IgG anti-toxin levels in these mice as a function of time demonstrated that these preparations of microencapsulated SEB toxoid stimulated an anti-SEB toxin response which both initiated and peaked at distinctly different times as shown in FIG. 3. Each preparation stimulated a peak IgG titer of 409,600, but the microspheres formulated of 50:50 and 85:15 DL-PLG and 100:0 L-PLG resulted in this level being attained on days 50, 130 and 230, respectively.

Figure 4:
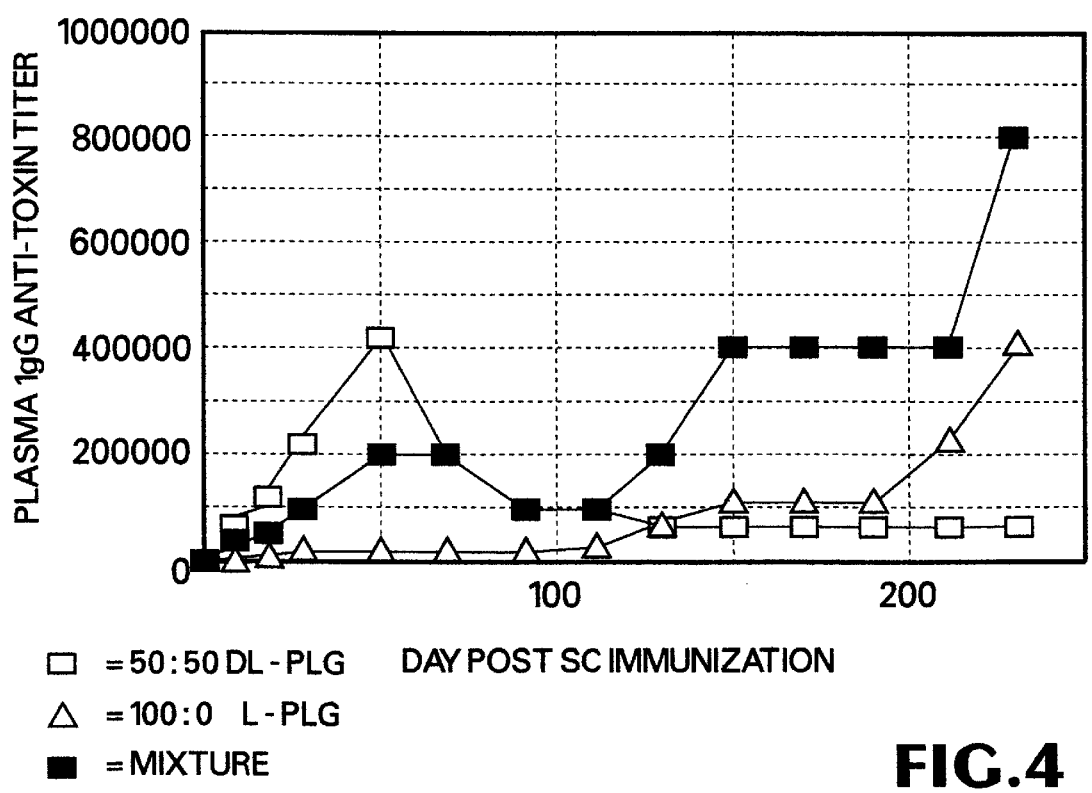
FIG. 4 represents the plasma IgG responses in mice following subcutaneous administration of 1–10 $\mu$m 50:50 DL-PLG, 100:0 L-PLG, and a mixture of 50:50 DL-PLG and 100:0 L-PLG SEB toxoid-containing microcapsules.

The possibility of using a blend of 1 to 10 $\mu$m microspheres with different DL-PLGs having different lactide/glycolide ratios to deliver discrete pulsed releases of antigen was investigated in a group of mice subcutaneously immunized in parallel. This blend consisted of 50:50 DL-PLG and 100:0 L-PLG microspheres in which each component contained 5 $\mu$g of SEB toxoid. The plasma IgG anti-SEB toxin response induced by this mixture was distinctly biphasic and exhibited both primary and secondary components as shown in FIG. 4. The first component of this response was coincident with that seen in mice which received only the 50:50 DL-PLG microspheres, while the second component coincided with the time at which the immune response was observed in mice receiving only the 100:0 L-PLG microspheres. The anamnestic character of the second phase indicates that distinct primary and secondary anti-SEB toxin responses have been induced.

These data show that in a mixture of microspheres with differing lactide/glycolide ratios, the degradation rate of an individual microsphere is a function of its lactide/glycolide ratio and that it is independent of the degradation rate of the other microspheres in the mixture. This finding indicates that 1) the time at which any vaccine pulse can be delivered is continuously variable across the range of lactide/glycolide rations, 2) the pulsed vaccine release profiles of any combination of microspheres with differing lactide/glycolide ratios can be predicted with a high degree of certainty based on the behavior of the individual components, and 3) the delay in vaccine release possible with microspheres <10 $\mu$m in diameter is up to approximately 8 months while the delay possible for microspheres >10 $\mu$m is up to approximately 2 years, allowing for any number of discrete pulsatile vaccine releases over these time frames.

Therefore, there exist a number of possible approaches to vaccination by the injectable microcapsules of the present invention. Among these include multiple injections of small microcapsules, preferably 1 to 5 micrometers, that will be engulfed by macrophages and obviate the need for immunopotentiators, as well as mixtures of free antigen for a primary response in combination with microcapsulated antigen in the form of microcapsules having a diameter of 10 micrometers or greater that release the antigen pulsatile to potentiate secondary and tertiary responses and provide immunization with a single administration. Also, a combination of small microcapsules for a primary response and larger microcapsules for secondary and later responses may be used, thereby obviating the need for both immunopotentiators and multiple injections.

B. Vaccine-Microcapsules Administered Orally

EXAMPLE 1

Orally-Administered Microspheres Containing TNP-KLH Induce Concurrent Circulating and Mucosal Antibody Responses to TNP Microcapsules containing the haptenated protein antigen trinitrophenyl-keyhole limpet hemocyanin (TNP-KLH) were prepared using 50:50 DL-PLG as the excipient. These microcapsules were separated according to size and those in the range of 1 to 5 micrometers in diameter were selected for evaluation. These microcapsules contained 0.2% antigen by weight. Their ability to serve as an effective antigen delivery system when ingested was tested by administering 0.5 mL of a 10 mg/mL suspension (10 micrograms antigen) in bicarbonate-buffered sterile tap water via gastric incubation on 4 consecutive days. For comparative purposes an additional group of mice was orally immunized in parallel with 0.5 mL of 20 micrograms/mL solution of unencapsulated TNP-KLH. Control mice were orally administered diluent only.

On Days 14 and 28 following the final immunization, serum, saliva and gut secretions were obtained from 5 fasted mice in each group. These samples were tested in isotype-specific radioimmunoassays to determine the levels of TNP-specific and total antibodies of the IgM, IgG and IgA isotypes (Table 13). The samples of saliva and gut secretions contained antibodies which were almost exclusively of the IgA class. These results are consistent with previous studies and provide evidence that the procedures employed to collect these secretions do not result in contamination with serum. None of the immunization protocols resulted in significant changes in the total levels of immunoglobulins present in any of the fluids tested. Low but detectable levels of naturally-occurring anti-TNP antibodies of the IgM and IgG isotypes were detected in the serum and of the IgA isotype in the serum and gut secretions of sham immunized control mice. However, the administration of 30 micrograms of microencapsulated TNP-KLH in equal doses over 3 consecutive days resulted in the appearance of significant antigen-specific IgA antibodies in the secretions, and of all isotypes in the serum by Day 14 after immunization (see the last column of Table 13). These antibody levels were increased further on Day 28. In contrast, the oral administration of the same amount of unencapsulated antigen was ineffective at inducing specific antibodies of any isotype in any of the fluids tested.

These results are noteworthy in several respects. First, significant antigen-specific IgA antibodies are induced in the serum and mucosal secretions, a response which is poor or absent following the commonly used systemic immunization methods. Therefore, this immunization method would be expected to result in significantly enhanced immunity at the mucosa; the portal of entry or site of pathology for a number of bacterial and viral pathogens. Secondly, the microencapsulated antigen preparation was an effective immunogen when orally administered, while the same amount of unencapsulated antigen was not. Thus, the microencapsulation resulted in a dramatic increase in efficacy, due to targeting of and increased uptake by the Peyer's patches. Thirdly, the inductive phase of the immune response appears to be of long duration. While systemic immunization with protein antigens in the absence of adjuvants is characterized by a peak in antibody levels in 7 to 14 days, the orally administered antigen-containing microcapsules induced responses were higher at Day 28 than Day 14. This indicates that bioerosion of the wall materials and release of the antigen is taking place over an extended period of time, and thus inducing a response of greater duration.

EXAMPLE 2
Orally Administered Microcapsules Containing SEB Toxoid Induce Concurrent Circulating and Mucosal Anti-SEB Toxin Antibodies The results presented above which show that (a) strong adjuvant activity is imparted by microencapsulation, and (b) microcapsules <5 micrometers in diameter disseminate to the mesenteric lymph nodes and spleen after entering through the Payer's patches, suggested that it would be feasible to induce a systemic immune response by oral immunization with vaccine incorporated into appropriately sized biodegradable microcapsules. This possibility was confirmed in experiments in which groups of mice were immunized with 100 micrograms of Staphylococcal enterotoxoid B in soluble form or within microcapsules with a 50:50 DL-PLG excipient. These mice were administered the soluble or microencapsulated toxoid via gastric tube on three occasions separated by 30 days, and plasma samples were obtained on Days 10 and 20 following each immunization. The data presented in Table 14 show the plasma end point titers of the IgM and IgG anti-toxin responses for the Day 20 time point after the primary, secondary and tertiary oral immunizations.

Mice receiving the vaccine incorporated in microcapsules exhibited a steady rise in plasma antibodies specific to the toxin with each immunization while soluble enterotoxoid was ineffective. This experiment employed the same lot of microcapsules and was performed and assayed in parallel with the experiments presented in Tables 4, 5 and 6 above. Therefore, these data directly demonstrate that oral immunization with microencapsulated Staphylococcal enterotoxoid B is more effective at inducing a serum anti-toxin response than is the parenteral injection of the soluble enterotoxoid at its optimal dose.

The secretory IgA response was examined in the same groups of mice. It was reasoned that the characteristics of this lot of enterotoxoid-containing microcapsules, a heterogeneous size range from <1 micrometer to approximately 10 micrometers, made it likely that a proportion of the microcapsules released the toxoid while fixed in the Peyer's patches. Therefore, on Days 10 and 20 following the tertiary oral immunization saliva and gut wash samples were obtained and assayed for toxin-specific antibodies of the IgA isotype (Table 15). In contrast to the inability of the soluble toxoid to evoke a response when administered orally, the ingestion of an equal amount of the toxoid vaccine incorporated into microcapsules resulted in a substantial sIgA anti-toxin response in both the saliva and gut secretions. It should be pointed out that the gut secretions from each mouse are diluted into a total of 5 mL during collection. Although it is difficult to determine the exact dilution factor this imposes on the material collected, it is safe to assume that the sIgA concentration is at minimum 10-fold higher in the mucus which bathes the gut, and this has not been taken into account in the measurements present here.

These data clearly demonstrate the efficacy of microencapsulated enterotoxoid in the induction of a sIgA anti-toxin response in both the gut and at a distant mucosal site when administered orally. Furthermore, through the use of a mixture of microcapsules with a range of diameters from <1 to 10 micrometers it is possible to induce this mucosal response concomitant with a strong circulating antibody response. This suggests that a variety of vaccines can be made both more effective and convenient to administer through the use of microencapsulation technology.

C. Vaccine Microcapsules Administered Intratracheally

EXAMPLE 1
Intratracheally Administered Microcapsules Containing SEB Toxoid Induce Concurrent Circulating and Mucosal Anti-Toxin Antibodies Folliculi lymphatic aggregati similar to the Peyer's patches of the gastrointestinal tract are present in the mucosally-associated lymphoid tissues found at other anatomical locations, such as the respiratory tract. Their function is similar to that of the Peyer's patches in that they absorb materials from the lumen of the lungs and are inductive sites for antibody responses which are characterized by a high proportion of sIgA. The feasibility of immunization through the bronchial-associated lymphoid tissue was investigated. Groups of mice were administered 50 microliters of PBS containing 50 micrograms of SEB toxoid in either microencapsulated or nonencapsulated form directly into the trachea. On days 10, 20, 30 and 40 following the immunization, samples of plasma, saliva, gut washings and bronchial-alveolar washings were collected.

Assay of the plasma samples for anti-toxin specific antibodies revealed that the administration of free SEB toxoid did not result in the induction of a detectable antibody response in any isotype (Table 16). In contrast, intratracheal instillation of an equal dose of microencapsulated SEB vaccine elicited toxin specific antibodies of all isotypes. This response reached maximal levels on Day 30 and was maintained through day 40 with IgM, IgG and IgA titers of 400, 51,300 and 400, respectively.

Similar to the responses observed in the plasma, toxin-specific antibodies in the bronchial-alveolar washings were induced by the microencapsulated toxoid, but not by the nonencapsulated vaccine (Table 17). The kinetics of the appearance of the anti-toxin antibodies in the bronchial secretions was delayed somewhat as compared to the plasma response in that the Day 20 response was only detected in the IgG isotype and was low in comparison to the plateau levels eventually obtained. However, maximal titers of IgG and IgA anti-toxin antibodies (1,280 and 320, respectively) were attained by Day 30 and were maintained through Day 40. No IgM class antibodies were detected in the bronchial-alveolar washings using this immunization method, a result consistent with the absence of IgM secreting plasma cells in the lungs and the inability of this large antibody molecule to transudate from the serum past the approximately 200,000 molecular weight cut off imposed by the capillary-alveolar membrane.

These data demonstrate that microencapsulation allowed an immune response to take place against the antigen SEB toxoid following administration into the respiratory tract while the nonencapsulated antigen was ineffective. This response was,observed both in the circulation and in the secretions bathing the respiratory tract. It should be noted that this immunization method was effective at inducing the appearance of IgA class antibodies. This antibody is presumably the product of local synthesis in the upper respiratory tract, an area which is not protected by the IgG class antibodies which enter the lower lungs from the blood circulation. Thus, intratracheal immunization with microencapsulated antigens, through the inhalation of aerosols, will be an effective means of inducing antibodies which protect the upper respiratory tract.

D. Vaccine Microcapsules Administered by Mixed Immunization Routes

In both man and animals, it has been shown that systemic immunization coupled with mucosal presentation of antigen is more effective than any other combination in promoting mucosal immune responses (Pierce, N. F. and Gowans, J. L. Cellular kinetics of the intestinal immune response to cholera toxoid in rats. J. Exp. Med. 142:1550; 1975). Three groups of mice were primed by IP immunization with 100 micrograms of microencapsulated SEB toxoid and 30 days later were challenged with 100 micrograms of microencapsulated SEB toxoid by either the IP, oral or IT routes. This was done to directly determine if a mixed immunization protocol utilizing microencapsulated antigen was advantageous with respect to the levels of sIgA induced.

Twenty days following the microencapsulated booster immunizations, samples of plasma, gut washings and bronchial-alveolar washings were obtained and the levels and isotype distribution of the anti-SEB toxin antibodies were determined in endpoint titration radioimmunoassays (Table 18). The IP boosting of IP primed mice led to the appearance of high levels of IgG anti-toxin antibodies in the samples of plasma and secretions, but was completely ineffective at the induction of detectable IgA antibodies in any fluid tested. In contrast, secondary immunization with microencapsulated SEB toxoid by either the oral or IT routes efficiently boosted the levels of specific IgG antibodies in the plasma (pre-secondary immunization titer in each group was 51,200) and also induced the appearance of significant levels of sIgA antibodies in the gut and bronchial-alveolar washings. Oral boosting of IP primed mice induced sIgA anti-SEB toxin antibodies to be secreted into the gut secretions at levels which were comparable with those requiring three spaced oral immunizations (Table 18 as compared to Table 15). Intratracheal boosting of previously IP immunized mice was particularly effective in the induction of a disseminated mucosal response and elicited the appearance of high concurrent levels of IgG and sIgA antibodies in both the samples of bronchial-alveolar and gut secretions.

These results are particularly important with respect to immunization against numerous infectious agents which exert their pathophysiologic effects through acute infections localized to the respiratory tract. Antibodies present within the respiratory tract originate from two different sources. Secretory IgA predominates in the mucus which bathes the nasopharynx and bronchial tree (Soutar, C. A. Distribution of plasma cells and other cells containing immunoglobulin in the respiratory tract of normal man and class of immunoglobulin contained therein. Thorax 31:58; 1976 and Kaltreider, H. B. and Chan, M. K. L. The class-specified immunoglobulin composition of fluids obtained from various levels of canine respiratory tract. J. Immunol. 116:423; 1976) and is the product of local plasma cells which are located in the lamina propria of the upper respiratory tract. In contrast to the nasopharynx and bronchial tree, the bronchioli and alveoli predominantly contain IgG which is passively-derived from the blood circulation via transudation (Reynolds, H. Y. and Newball, H. H. Analysis of proteins and respiratory cells obtained from human lungs by bronchial lavage. J. Lab. Clin. Med. 84:559; 1974). Thus, effective protection of the lungs requires both circulating IgG and mucosal sIgA antibodies.

These data indicate that mixed route immunization protocols utilizing microencapsulated antigens will prove the most efficient in the induction of concurrent circulating and mucosal antibody responses. Although the experiments reported here examine discrete priming and boosting steps which each required an administration of microencapsulated antigen, it will be possible to use the flexibility in controlled pulsatile release afforded by the microcapsule delivery system to design a single time of administration regimen which will stimulate maximum concurrent systemic and secretory immunity. As an example, microencapsulated antigen could be administered by both injection and ingestion during a single visit to a physician. By varying the lactide to glycolide ratio in the two doses, the systemically administered dose could be released within a few days to prime the immune system, and the second (oral) dose could be released in the Peyer's patches at a later time to stimulate a boosted mucosal response.

IV. ABSORPTION OF PHARMACEUTICALS

The following example shows that small microcapsules (less than 5 micrometers, preferably 1 to 5 microns) can also improve the absorption of pharmaceuticals as well as antigens into the body. Etretinate, (All-E)-9-(4-methoxy-2,3,6, -trimethyl) phenyl-3, 7-dimethyl-2,4,8-nonatetraenoic acid, ethyl ester) was microencapsulated in 50:50 poly(DL-lactide-co-glycolide). The microcapsules were 0.5 to 4 micrometers in diameter and contained 37.2 wt % etretinate. These etretinate microcapsules, as well as unencapsulated etretinate, was administered to mice by oral gavage using 1 wt % Tween 80 in water as a vehicle. Only single doses of 50 mg etretinate/kg were given. Blood from the dosed mice was collected at specific time intervals and the serum of this blood was quantified for etretinate and/or its metabolites using a high performance chromatographic procedure (Table 19). The results show that mice treated with the,etretinate microcapsules had significantly higher blood levels of etretinate than mice treated with unencapsulated etretinate. Like the less than 5-micrometer vaccine microcapsules, it is believed that the microcapsules carry the etretinate to the blood stream via the lymphoidal tissue (Peyer's patches) in the gastrointestinal tract. This same approach should be applicable to increasing the absorption of other drugs, where its application would be especially useful for the delivery of biological pharmaceuticals such as peptides, proteins, nucleic acids, and the like.

TABLE 1

Penetration of Coumarin-6 85:15 DL-PLG Microspheres Into and Through the Peyer's Patches Following Oral Administration

| Time (days) | Total number observed | Proportion of diameter (%) Small <2 um | Medium 2–5 um | Large >5 um | Proportion at location (%) Dome | Deep |
|---|---|---|---|---|---|---|
| 1 | 296 | 47 | 35 | 18 | 92 | 8 |
| 2 | 325 | 45 | 32 | 23 | 83 | 17 |
| 4 | 352 | 46 | 31 | 23 | 76 | 24 |
| 7 | 196 | 21 | 29 | 41 | 88 | 11 |
| 14 | 148 | 16 | 29 | 55 | 98 | 2 |
| 21 | 91 | 7 | 27 | 66 | 98 | 2 |
| 28 | 63 | 5 | 24 | 71 | 100 | 0 |
| 35 | 52 | 6 | 19 | 79 | 97 | 3 |

TABLE 2

Migration of Coumarin-6 85:15 DL-PLG Microspheres Into and Through the Mesenteric Lymph Nodes Following Oral Administration

| Time (days) | Total number observed | Proportion of diameter (%) Small <2 um | Medium 2–5 um | Large >5 um | Proportion at location (%) Dome | Deep |
|---|---|---|---|---|---|---|
| 1 | 8 | 50 | 50 | 0 | 100 | 0 |
| 2 | 83 | 76 | 24 | 0 | 95 | 5 |
| 4 | 97 | 73 | 27 | 0 | 73 | 27 |
| 7 | 120 | 67 | 32 | 0 | 64 | 36 |
| 14 | 54 | 83 | 17 | 0 | 9 | 91 |
| 21 | 20 | 75 | 25 | 0 | 5 | 95 |
| 28 | 15 | 67 | 32 | 0 | 0 | 100 |
| 35 | 9 | 44 | 56 | 0 | 0 | 100 |

TABLE 3

Targeted Absorption of 1- to 10-μm Microspheres with Various Excipients by the Peyer's Patches of the Gut-Associated Lymphoid Tissues Following Oral Administration

| Microsphere Excipient | Biodegradable | Absorption by the Peyer's patches |
|---|---|---|
| Poly(styrene) | No | Very Good |
| Poly(methyl methacrylate) | No | Very Good |
| Poly(hydroxybutyrate) | Yes | Very Good |
| Poly(DL-lactide) | Yes | Good |
| Poly(L-lactide) | Yes | Good |
| 85:15 Poly(DL-lactide-co-glycolide) | Yes | Good |
| 50:50 Poly(DL-lactide-co-glycolide) | Yes | Good |
| Cellulose acetate hydrogen phthalate | No | None |
| Cellulose triacetate | No | None |
| Ethyl cellulose | No | None |

TABLE 4

Primary Anti-Toxin Response to Microencapsulated Versus Soluble Staphylococcal Enterotoxoid B

| Toxoid Dose (μg) | Form | Plasma Anti-Toxin Titer Day 20 IgM | IgG | Day 10 IgM | IgG |
|---|---|---|---|---|---|
| 100 | Microencapsulated | 1,280 | 320 | 1,280 | 10,240 |
| 50 | Microencapsulated | 640 | 320 | 1,280 | 5,120 |
| 25 | Microencapsulated | 320 | <20 | 640 | 2,560 |
| 50 | Soluble | <20 | <20 | <20 | <20 |
| 25 | Soluble | 320 | <20 | 160 | <20 |
| 12.5 | Soluble | 40 | <20 | <20 | <20 |

TABLE 5

Secondary Anti-Toxin Response to Microencapsulated Versus Soluble Staphylococcal Enterotoxoid B

| Toxoid Dose (μg) per Immunization | Form | Plasma Anti-Toxin Titer Day 10 IgM | IgG | Day 20 IgM | IgG |
|---|---|---|---|---|---|
| 100 | Microencapsulated | 320 | 163,840 | 160 | 81,920 |
| 50 | Microencapsulated | 640 | 81,920 | 640 | 163,840 |
| 25 | Microencapsulated | 2,560 | 40,960 | 640 | 81,920 |
| 50 | Soluble | 160 | <20 | 80 | <20 |
| 25 | Soluble | 320 | 160 | 160 | 320 |
| 12.5 | Soluble | 160 | 40 | 40 | 80 |

TABLE 6

Tertiary Anti-Toxin Response to Microencapsulated Versus Soluble Staphylococcal Enterotoxoid B

| Toxoid Dose (μg) per Immunization | Form | Plasma Anti-Toxin Titer Day 10 IgM | IgG | Day 20 IgM | IgG |
|---|---|---|---|---|---|
| 100 | Microencapsulated | 1,280 | 655,360 | 640 | 327,680 |
| 50 | Microencapsulated | 2,560 | 327,680 | 280 | 327,680 |
| 25 | Microencapsulated | 2,560 | 327,680 | 640 | 163,840 |
| 50 | Soluble | 640 | 1,280 | 640 | 640 |
| 25 | Soluble | 320 | 10,240 | 80 | 10,240 |
| 12.5 | Soluble | 160 | 1,280 | 40 | 1,280 |

TABLE 7

Primary Systemic Anti-Toxin Response Induced by Various Parenteral Immunization Routes

| Dose (μg) of Microencapsulated Toxoid | Immunization Route | Plasma IgG Anti-Toxin Titer Day 15 | Day 30 | Day 45 |
|---|---|---|---|---|
| 100 | Intraperitoneal | 12,800 | 102,400 | 204,800 |
| 100 | Subcutaneous | 6,400 | 25,600 | 204,800 |

TABLE 8

Secondary Systematic Anti-Toxin Response Induced by Various Parenteral Immunization Routes

| Dose (μg) Microencapsulated Toxoid per | Immunization | Plasma IgG Anti-Toxin Titer |
|---|---|---|

| Immunization | Routes | Day 15 | Day 30 | Day 45 |
|---|---|---|---|---|
| 100 | IP - IP | 819,200 | 1,638,400 | 3,276,800 |
| 100 | SC - SC | 409,600 | 819,200 | 3,276,800 |

TABLE 9

Microspheres Do not Possess Inherent Adjuvant Activity

| Dose (μg) of Toxoid | Form | Plasma Anti-Toxin Titer | | | | | |
|---|---|---|---|---|---|---|---|
| | | Day 10 | | Day 20 | | Day 30 | |
| | | IgM | IgG | IgM | IgG | IgM | IgG |
| 25 | Antigen in Microspheres | 6,400 | 6,400 | 400 | 12,800 | 800 | 25,600 |
| 25 | Soluble Antigen | 800 | <50 | 200 | 800 | 100 | <50 |
| 25 | Antigen plus Placebo | 800 | <50 | 200 | <50 | 200 | 50 |

TABLE 10

Systemic Anti-Toxic Response Induced by Parenteral Immunization μm Microspheres Releasing Antigen at Various Rates

| Dose (μg) of Toxoid | Form | Lactide/ Glycolide Ratio | Antigen release at 48 Hr | Plasma IgG Anti-Toxin Titer on Day | | | | | |
|---|---|---|---|---|---|---|---|---|---|
| | | | | 10 | 15 | 20 | 30 | 45 | 60 |
| 100 | Soluble | — | — | <50 | <50 | <50 | <50 | <50 | <50 |
| 100 | Microspheres | 50:50 | 60% | 400 | — | 6,400 | 3,200 | — | — |
| 100 | Microspheres | 50:50 | 30% | 400 | — | 12,800 | 6,400 | — | — |
| 100 | Microspheres | 50:50 | 10% | — | 6,400 | — | 102,400 | 102,400 | 51,200 |
| 100 | Microspheres | 85:15 | 0% | — | 3,200 | — | 51,200 | 102,400 | 102,400 |

TABLE 11

Results of CPE Inhibition Assays on Serum Samples from the JE Vaccine Immunization Studies

| Animal | Dilution of serum capable of reducing virus-induced CPE by 50% on Day | | |
|---|---|---|---|
| | 21 | 49 | 77 |
| Group 1 = Untreated Control | | | |
| GMT[a] | <10 | 11 | 11 |
| Average | <10 | 11 | 11 |
| Maximum | <10 | 16 | <20 |
| Minimum | <10 | <10 | <10 |
| Group 2 = 3.0 mg unencapsulated JE vaccine IP on Day 10 | | | |
| GMT | 44 | 73 | 50 |
| Average | 55 | 95 | 71 |
| Maximum | 127 | 254 | 160 |
| Minimum | <10 | 13 | <10 |
| Group 3 = 3.0 mg unencapsulated JE vaccine IP on Days 0, 14 and 42 | | | |
| GMT | 507 | 3,880 | 1,576 |
| Average | 934 | 5,363 | 2,951 |
| Maximum | 4,064 | >10,240 | >10,240 |
| Minimum | 160 | 806 | 254 |
| Group 4 = 3.0 mg unencapsulated + 3.0 mg microencapsulated JE vaccine IP on Day 0 | | | |
| GMT | 77 | 718 | 1,341 |
| Average | 803 | 1,230 | 2,468 |
| Maximum | 320 | 5,120 | 10,240 |
| Minimum | 13 | 160 | 254 |

[a]GMT = Geometric mean titers.

TABLE 12

Results of Plaque-Reduction Assays on Pooled Serum Samples from the JE Vaccine Immunization Studies

| Group | Treatment | Day | Serum dilution to reach | |
|---|---|---|---|---|
| | | | 50% endpoint | 80% endpoint |
| 1[a] | Controls | 0 | <10 | <10 |
| 1 | Controls | 14 | <10 | <10 |
| 1 | Controls | 21 | <10 | <10 |
| 1 | Controls | 42 | <10 | <10 |
| 1 | Controls | 49 | <10 | <10 |
| 1 | Controls | 84 | <10 | <10 |
| 2 | Unencapsulated JE | 0 | <10 | <10 |
| 2[b] | Unencapsulated JE | 14 | 160 | 20 |
| 2 | Unencapsulated JE | 21 | ND[c] | ND |
| 2 | Unencapsulated JE | 42 | 320 | 80 |
| 2 | Unencapsulated JE | 49 | 320 | 40 |
| 2 | Unencapsulated JE | 84 | 640 | 160 |
| 3[d] | Unencapsulated JE | 0 | <10 | <10 |
| 3 | Unencapsulated JE | 14 | 160 | 40 |
| 3 | Unencapsulated JE | 21 | 2,560 | 640 |
| 3 | Unencapsulated JE | 42 | 1,280 | 640 |
| 3 | Unencapsulated JE | 49 | 5,120 | 2,560 |
| 3 | Unencapsulated JE | 84 | 2,560 | 1,280 |
| 4[e] | Microencapsulated JE | 0 | <10 | <10 |
| 4 | Microencapsulated JE | 14 | 160 | 20 |
| 4 | Microencapsulated JE | 21 | 320 | 80 |
| 4 | Microencapsulated JE | 42 | 5,120 | 640 |

TABLE 12-continued

Results of Plaque-Reduction Assays on Pooled Serum
Samples from the JE Vaccine Immunization Studies

| | | | Serum dilution to reach | |
|---|---|---|---|---|
| Group | Treatment | Day | 50% endpoint | 80% endpoint |
| 4 | Microencapsulated JE | 49 | 5,120 | 640 |
| 4 | Microencapsulated JE | 84 | 10,000 | 2,560 |

[a]Untreated controls.
[b]Animals received 3.0 mg of unencapsulated JE vaccine IP on Day 0.
[c]ND = Not determined (insufficient sample quantity).
[d]Animals received 3.0 mg of unencapsulated JE vaccine IP on Day 0, 14 and 42.
[e]Animals received 3.0 mg of unencapsulated and 3.0 mg of microencapsulated JE vaccine IP on Day 0.

TABLE 15

Toxin-Specific IgA Antibodies in the Saliva and Gut
Fluids of Mice of Days 10 and 20 After Tertiary Oral Immunization
with Soluble or Microencapsulated Enterotoxoid

| Enterotoxoid | | IgA anti-enterotoxin titer following tertiary oral immunization | | | |
|---|---|---|---|---|---|
| | | Day 10 | | Day 20 | |
| dose ($\mu$g) per immunization | Form | Saliva | Gut Wash | Saliva | Gut Wash |
| 100 | Microspheres | 1,280 | 1,024 | 640 | 256 |
| 100 | Soluble | 40 | <8 | 10 | <8 |

TABLE 13

The Induction of TNP-Specific Antibodies in the Serum Mucosal Secretions
of BALB/C Mice by Oral Immunization with Microencapsulated TNP-KLH

| | | | ng Immunoglobulin/mL sample | | | | | |
|---|---|---|---|---|---|---|---|---|
| | | | IgM | | IgG | | IgA | |
| Immunogen | Time after immunization | Biologic sample | Total | Anti-TNP | Total | Anit-TNP | Total | Anti-TNP |
| Control | Day 14 | Gut wash | <1 | <1 | 62 | <1 | 79,355 | 25 |
| | | Saliva | <40 | <10 | <40 | <10 | 2,651 | <10 |
| | | Serum | 445,121 | 6 | 5,503,726 | 37 | 1,470,553 | 32 |
| Unencapsulated TNP-KLH | Day 14 | Gut wash | 4 | 1 | 131 | <1 | 64,985 | 17 |
| | | Salvia | <40 | <10 | <40 | <10 | 1,354 | <10 |
| | | Serum | 298,733 | 11 | 6,000,203 | 29 | 1,321,986 | 21 |
| TNP-KLH Microcapsules | Day 14 | Gut wash | 3 | <1 | 130 | <1 | 95,368 | 222 |
| | | Saliva | <40 | <10 | <40 | <10 | 1,461 | 88 |
| | | Serum | 360,987 | 1,461 | 5,312,896 | 572 | 1,411,312 | 1,077 |
| Unencapsulated TNP-KLH | Day 28 | Gut wash | <1 | <1 | 94 | <1 | 88,661 | 64 |
| | | Saliva | <40 | <10 | <40 | <10 | 1,278 | <10 |
| | | Serum | 301,223 | 21 | 5,788,813 | 67 | 1,375,322 | 63 |
| TNP-KLH Microcapsules | Day 28 | Gut wash | 4 | <1 | 122 | 2 | 82,869 | 422 |
| | | Saliva | <40 | <10 | <40 | <10 | 1,628 | 130 |
| | | Serum | 320,192 | 1,904 | 5,591,503 | 2,219 | 1,277,505 | 1,198 |

TABLE 14

Plasma IgM and IgG Anti-Toxin Levels on Day 20
Following Primary, Secondary, and Tertiary Oral Immunization with
Soluble or Microencapsulated (50:50 DL-PLG) Staphylococcal Toxoid

| Enterotoxoid | | Plasma anti-toxin titer on day 20 following oral immunization | | | | | |
|---|---|---|---|---|---|---|---|
| | | Primary | | Secondary | | Tertiary | |
| does ($\mu$g) per immunization | Form | IgM | IgG | IgM | IgG | IgM | IgG |
| 100 | Microspheres | 80 | 1,280 | 320 | 5,120 | 1,280 | 40,960 |
| 100 | Soluble | <20 | <20 | 80 | <20 | 640 | <20 |

TABLE 16

Serum Anti-Toxin Antibody Levels Induced Through Intratracheal Immunization with
Soluble or Microencapsulated Staphylococcal Enterotoxin B Toxoid

| Enterotoxoid | | Plasma anti-toxin of day following intratracheal immunization | | | | | | | | | | |
|---|---|---|---|---|---|---|---|---|---|---|---|---|
| | | 10 | | | 20 | | | 30 | | | 40 | | |
| dose (μg) | Form | IgM | IgG | IgA | IgM | IgG | IgA | IgM | IgG | IgA | IgM | IgG | IgA |
| 50 | Microencapsulated | <50 | <50 | <50 | 200 | 25,600 | 400 | 400 | 51,200 | 400 | 200 | 51,200 | 400 |
| 50 | Soluble | <50 | <50 | <50 | <50 | <50 | <50 | <50 | <50 | <50 | <50 | <50 | <50 |

TABLE 17

Bronchial-Alveolar Washing Antibody Levels Induced Through Intratracheal
Immunization with Soluble or Microencapsulated Staphylococcal Enterotoxin B Toxoid

| Enterotoxoid | | Bronchial-alveolar washing anti-toxin titer on day following intratracheal immunization | | | | | | | | | | | |
|---|---|---|---|---|---|---|---|---|---|---|---|---|
| | | 10 | | | 20 | | | 30 | | | 40 | | |
| dose (μg) | Form | IgM | IgG | IgA | IgM | IgG | IgA | IgM | IgM | IgA | IgM | IgG | IgA |
| 50 | Microencapsulated | <5 | <5 | <5 | <5 | 80 | <5 | <5 | 1,280 | 320 | <5 | 1,280 | 320 |
| 50 | Soluble | <5 | <5 | <5 | <5 | <5 | <5 | <5 | <5 | <5 | <5 | 20 | 50 |

TABLE 18

Anti-SEB Toxin Antibody Responses Induced in Various Biological Fluids
by Mixed Route Immunization Protocols Using Microencapsulated SEB Toxoid

| Route of Immunization | | Dose of Microencapsulated SEB toxoid per Immunization (μg) | Anti-toxin titer on day 20 following secondary immunization | | | | | | | | |
|---|---|---|---|---|---|---|---|---|---|---|---|
| | | | Plasma | | | Gut Wash | | | Bronchial Wash | | |
| Primary | Secondary | | IgM | IgG | IgA | IgM | IgG | IgA | IgM | IgG | IgA |
| 1P | 1P | 100 | 3,200 | 1,638,400 | <50 | <20 | 10,240 | <20 | <5 | 10,240 | <5 |
| 1P | Oral | 100 | 1,600 | 204,800 | <50 | <20 | 640 | 640 | <5 | 2,560 | 1,280 |
| 1P | 1T | 100 | 1,600 | 819,200 | <50 | <20 | 2,560 | 2,560 | <5 | 20,480 | 2,560 |

TABLE 19

Concentration of Etretinate in Mouse Serum After Oral
Dosing with Microencapsulated and Unencapsulated Etretinate

| | Etretinate Concentration, ng/mL | |
|---|---|---|
| Times/hr | Microcapsules | Uncapsulated Drug |
| 1 | 4,569 | 191 |
| 3 | 634 | 158 |
| 6 | 242 | <31 |
| 24 | ND | ND |

ND = None detected

What is claimed is:

1. A method of delivering a bioactive agent to the mucosally associated lymphoreticular tissues of an animal, comprising administering microcapsules to said animal so that an immunogenically effective amount of said microcapsules reach and are selectively taken up by said mucosally associated lymphoreticular tissues, wherein said microcapsules comprise said agent encapsulated in a biocompatible excipient and wherein said microcapsules are of a size of between approximately 1 micrometer and approximately 10 micrometers.

2. The method of claim 1, wherein said bioactive agent is a drug, nutrient, immunomodulator, lymphokine, monokine, cytokine, or antigen.

3. The method of claim 1, wherein said bioactive agent is an antigen.

4. The method of claim 3, wherein said antigen is an allergen, viral antigen, bacterial antigen, protozoan antigen, or a fungal antigen.

5. The method of claim 3, wherein said antigen is an influenzae antigen, Staphylococcus antigen, respiratory syncytial antigen, parainfluenza virus antigen, *Hemophilus influenza* antigen, *Bordetella pertussis* antigen, *Neisseria gonorrhoea* antigen, *Streptococcus pneumoniae* antigen, *Plasmodium falciparum* antigen, helminthic pathogen antigen, or an antigen to vaccinate against allergies.

6. The method of claim 3, wherein said antigen is an influenza virus or staphylococcal enterotoxin B.

7. The method of claim 3, wherein said bioactive agent further includes a cytokine.

8. The method of claim 7, wherein said bioactive agent further includes an adjuvant.

9. The method of claim 1, wherein said bioactive agent is a mixture of a cytokine and an adjuvant.

10. The method of claim 1, wherein said bioactive agent comprises a peptide, protein or nucleic acid.

11. The method of claim 1, wherein said administering is by oral, nasal, rectal, vaginal, ophthalmical, or oral inhalation administration.

12. The method of claim 1, wherein said biocompatible excipient is a poly(lactide-co-glycolide), poly(lactide), poly (glycolide), copolyoxalate, polycaprolactone, poly(lactide-co-caprolactone), poly(esteramide), polyorthoester, poly($\beta$-hydroxybutyric acid), polyanhydride, or a mixture thereof.

13. The method of claim 1, wherein said microcapsules comprise a plurality of first microcapsules having a size of between approximately 1 micrometer and approximately 5 micrometers and a plurality of second microcapsules having a size of between approximately 5 micrometers and approximately 10 micrometers, and wherein said administering comprises the delivery of a mixture of said first and second microcapsules to said animal to provide both systemic immunity and mucosal immunity.

14. The method of claim 1, wherein the delivery is orally and the mucosally associated lymphoeticular tissues are the Peyer's patch.

15. A method of delivering a bioactive agent to the mucosally associated lymphoreticular tissues of an animal, comprising administering microcapsules to said animal so that an immunogenically effective amount of said microcapsules reach and are selectively taken up by said mucosally associated lymphoreticular tissues, wherein said microcapsules comprise said agent encapsulated in a biocompatible excipient and wherein said microcapsules are of a size of less than approximately 10 micrometers.

16. The method of claim 15, wherein the delivery is orally and the mucosally associated lymphoeticular tissues are the Peyer's patch.

17. A method of providing systemic immunity in an animal, comprising administering microcapsules to said animal so that immunogenically effective amount of said microcapsules reach and are selectively taken up by the mucosally-associated lymphoreticular tissues to provide a systemic immune response in said animal, wherein said microcapsules comprise a bioactive agent encapsulated in a biocompatible excipient and wherein said microcapsules are of a size of between approximately 1 micrometer and approximately 5 micrometers.

18. The method of claim 17, wherein said bioactive agent is an immunomodulator, lymphokine, monokine, cytokine, or antigen.

19. The method of claim 17, wherein said bioactive agent is an antigen.

20. The method of claim 19, wherein said antigen is an allergen, viral antigen, bacterial antigen, protozoan antigen, or a fungal antigen.

21. The method of claim 19, wherein said antigen is an influenzae antigen, Staphylococcus antigen, respiratory syncytial antigen, parainfluenza virus antigen, *Hemophilus influenza* antigen, *Bordetella pertussis* antigen, *Neisseria gonorrhoea* antigen, *Streptococcus pneumoniae* antigen, *Plasmodium falciparum* antigen, helminthic pathogen antigen, or an antigen to vaccinate against allergies.

22. The method of claim 19, wherein said antigen is an influenza virus or staphylococcal enterotoxin B.

23. The method of claim 19, wherein said bioactive agent further includes a cytokine.

24. The method of claim 23, wherein said bioactive agent further includes an adjuvant.

25. The method of claim 17, wherein said bioactive agent is a mixture of a cytokine and an adjuvant.

26. The method of claim 17, wherein said bioactive agent comprises a peptide, protein or nucleic acid.

27. The method of claim 17, wherein said administering is by oral, nasal, rectal, vaginal, ophthalmical, or oral inhalation administration.

28. The method of claim 17, wherein said biocompatible excipient is a poly(lactide-co-glycolide), poly(lactide), poly (glycolide), copolyoxalate, polycaprolactone, poly(lactide-co-caprolactone), poly(esteramide), polyorthoester, poly($\beta$-hydroxybutyric acid), polyanhydride, or a mixture thereof.

29. A method of providing mucosal immunity in an animal, comprising administering microcapsules to said animal so that an immunogenically effective amount of said microcapsules reach and are selectively taken up by the mucosally-associated lymphoreticular tissues to provide a mucosal immune response in said animal, wherein said microcapsules comprise a bioactive agent encapsulated in a biocompatible excipient and wherein said microcapsules are of a size of between approximately 5 micrometers and approximately 10 micrometers.

30. The method of claim 29, wherein said bioactive agent is an immunomodulator, lymphokine, monokine, cytokine, or antigen.

31. The method of claim 29, wherein said bioactive agent is an antigen.

32. The method of claim 31, wherein said antigen is an allergen, viral antigen, bacterial antigen, protozoan antigen, or a fungal antigen.

33. The method of claim 31, wherein said antigen is an influenzae antigen, Staphylococcus antigen, respiratory syncytial antigen, parainfluenza virus antigen, *Hemophilus influenza* antigen, *Bordetella pertussis* antigen, *Neisseria gonorrhoea* antigen, *Streptococcus pneumoniae* antigen, *Plasmodium falciparum* antigen, helminthic pathogen antigen, or an antigen to vaccinate against allergies.

34. The method of claim 31, wherein said antigen is an influenza virus or staphylococcal enterotoxin B.

35. The method of claim 31, wherein said bioactive agent further includes a cytokine.

36. The method of claim 35, wherein said bioactive agent further includes an adjuvant.

37. The method of claim 29, wherein said bioactive agent is a mixture of a cytokine and an adjuvant.

38. The method of claim 29, wherein said bioactive agent comprises a peptide, protein or nucleic acid.

39. The method of claim 29, wherein said administering is by oral, nasal, rectal, vaginal, ophthalmical, or oral inhalation administration.

40. The method of claim 29, wherein said biocompatible excipient is a poly(lactide-co-glycolide), poly(lactide), poly (glycolide), copolyoxalate, polycaprolactone, poly(lactide-co-caprolactone), poly(esteramide), polyorthoester, poly($\beta$-hydroxybutyric acid), polyanhydride, or a mixture thereof.

41. A method of providing mucosal immunity in an animal, comprising administering effective amounts of microcapsules to said animal so that an immunogenically effective amount of said microcapsules reach and are selectively taken up by the mucosally-associated lymphoreticular tissues to provide a mucosal immune response in said animal, wherein said microcapsules comprise effective amounts of a bioactive agent encapsulated in a biocompatible excipient and wherein said microcapsules are of a size of between approximately 1 micrometer and approximately 5 micrometers.

42. The method of claim 41, wherein said bioactive agent is an immunomodulator, lymphokine, monokine, cytokine, or antigen.

43. The method of claim 41, wherein said bioactive agent is an antigen.

44. The method of claim 43, wherein said antigen is an allergen, viral antigen, bacterial antigen, protozoan antigen, or a fungal antigen.

45. The method of claim 43, wherein said antigen is an influenzae antigen, Staphylococcus antigen, respiratory syncytial antigen, parainfluenza virus antigen, *Hemophilus influenza* antigen, *Bordetella pertussis* antigen, *Neisseria gonorrhoea* antigen, *Streptococcus pneumoniae* antigen, *Plasmodium falciparum* antigen, helminthic pathogen antigen, or an antigen to vaccinate against allergies.

46. The method of claim 43, wherein said antigen is an influenza virus or staphylococcal enterotoxin B.

47. The method of claim 43, wherein said bioactive agent further includes a cytokine.

48. The method of claim 47, wherein said bioactive agent further includes an adjuvant.

49. The method of claim 41, wherein said bioactive agent is a mixture of a cytokine and an adjuvant.

50. The method of claim 41, wherein said bioactive agent comprises a peptide, protein, or nucleic acid.

51. The method of claim 41, wherein said administering is by oral, nasal, rectal, vaginal, ophthalmical, or oral inhalation administration.

52. The method of claim 41, wherein said biocompatible excipient is a poly(lactide-co-glycolide), poly(lactide), poly (glycolide), copolyoxalate, polycaprolactone, poly(lactide-co-caprolactone), poly(esteramide), polyorthoester, poly($\beta$-hydroxybutyric acid), polyanhydride, or a mixture thereof.

* * * * *